(12) United States Patent
Rantala

(10) Patent No.: US 6,432,051 B1
(45) Date of Patent: Aug. 13, 2002

(54) TONOMETRIC MEASURING HEAD AND MEASURING METHOD

(75) Inventor: Tor Börje Rantala, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/268,485

(22) Filed: Mar. 11, 1999

(30) Foreign Application Priority Data

Mar. 13, 1998 (FI) .................................................. 980560

(51) Int. Cl.[7] .................................................. A61B 5/00
(52) U.S. Cl. ........................ 600/364; 600/309; 600/351; 600/353
(58) Field of Search .................................. 600/338, 342, 600/353, 309, 311, 322, 345, 348, 355, 364, 351

(56) References Cited

U.S. PATENT DOCUMENTS

| | | | |
|---|---|---|---|
| 4,197,853 A | 4/1980 | Parker | |
| 4,643,192 A | 2/1987 | Fiddian-Green | |
| 4,932,410 A | 6/1990 | Lacourciere et al. | |
| 5,251,619 A | * 10/1993 | Lee ............................ | 600/350 |
| 5,479,923 A | 1/1996 | Rantala | |
| 5,526,809 A | 6/1996 | Fiddian-Green | |

FOREIGN PATENT DOCUMENTS

| | | |
|---|---|---|
| DE | 26 19 471 | 11/1977 |
| DE | 196 35 306 | 3/1998 |
| EP | 135840 | 4/1985 |
| EP | 440741 | 8/1991 |
| EP | 509310 | 10/1992 |
| EP | 575737 | 12/1993 |
| FI | 912032 | 4/1991 |
| FI | 921594 | 10/1992 |
| WO | 90/01893 | 3/1990 |
| WO | 91/07910 | 6/1991 |
| WO | 91/077910 | 6/1991 |
| WO | 95/03738 | 2/1995 |
| WO | 96/25090 | 8/1996 |
| WO | 97/37587 | 10/1997 |

* cited by examiner

Primary Examiner—Eric F. Winakur
(74) Attorney, Agent, or Firm—Andrus, Sceales, Starke & Sawall, LLP

(57) ABSTRACT

The invention relates to a tonometric measuring head for bringing a measuring medium to a composition consistent with an individual to be examined non-invasively through the outermost tissue layer. A measuring head comprises a sealed chamber, having a wall whose oppositely facing sides are essentially made of pliable membrane materials, at least one membrane material of said materials being permeable to a gas to be analyzed but effectively impermeable at least to solids and liquids, as well as a measuring medium in a cavity within the wall. The measuring head is provided with a guide member between the chamber and an external device. In addition, the chamber wall is partially constituted by a pliable second membrane material which is effectively impermeable both to a gas to be analyzed and to at least solids and liquids. The measuring head, along with its chamber, is flexible as a whole and areas, constituted by said membrane materials with considerably unequal permeabilities, are included in the oppositely facing sides. Thus, the composition of a measuring medium to be analyzed can be made asymmetrically dependent upon the body of only one individual in the contact conditions of two individuals.

56 Claims, 7 Drawing Sheets

TONOMETRIC MEASURING HEAD AND MEASURING METHOD

BACKGROUND OF THE INVENTION

The present invention relates to a tonometric measuring head for bringing an analyzable measuring medium to a composition consistent with an individual to be examined and non-invasively through the outermost tissue layer, said measuring head comprising: a substantially sealed chamber, having a wall whose oppositely facing sides are essentially made of pliable membrane materials, at least one of said materials comprising a pliable, first membrane material permeable to a gas to be analyzed but impermeable at least to solids and liquids; a measuring medium in a cavity within the chamber wall; at least one guide means extending between said chamber and an external device, said guide means and the chamber wall being tightly linked to each other. In addition, the invention relates to a method during parturition for monitoring non-invasively the prenatal and natal physical condition of a child, said method comprising the steps of: introducing an elongated and flat measuring instrument, provided with an active side and an inactive side, between a birth canal and a child; setting the measuring instrument, during said introduction, with its active side towards the child and its inactive side towards a wall of the birth canal; positioning the measuring instrument in such a way that its length reaches the area of a cervix uteri.

This type of sampling means have been described in publications U.S. Pat. No. 4,643,192, U.S. Pat. No. 5,526,809 and U.S. Pat. No. 5,479,923. All these publications disclose tonometric measuring heads provided with one or more spherical chambers, having walls which are permeable to a gas to be examined. In these publications, the gas to be analyzed is carbon dioxide and, furthermore, the first two publications necessitate the measurement of a bicarbonate concentration. According to the cited publications, such a tonometric sampling means is introduced into a lumen of the body of a patient to be examined, such as the stomach or intestines, whereby a gas to be examined diffuses from the patient through a wall of the tonometric sampling means into a liquid contained in the chamber. Thereafter, the liquid present within the sampling chamber is examined for its composition either by delivering it to a laboratory, which is the case in the first two publications, or by circulating it along one or two tubes extending between the sampling means and an external analyzer to detectors included in this analyzer. It is typical of all these tonometric measuring heads to follow the above-described principle in terms of introducing the same within a body cavity of the patient for a measuring procedure.

Monitoring a physical condition, such as the oxygen supply, of a presently delivered baby is known to be very difficult, as it is inconvenient to attach any measuring sensors to a prenatal or natal child. At the moment, a presently delivered child can be monitored either in a very old-fashioned manner by listening to heart sounds through the abdominal layers of a parturient or alternatively by an EKG-electrode screwed on the head of a baby for obtaining the heart rate, which roughly represents the baby's oxygen supply. These are quite inaccurate and unreliable methods. The publications EP-0,135,840, EP-0,575,737 and EP-0,509,310 only disclose pulse oximeter sensors, intended for monitoring the condition of a presently delivered baby by placing the same alongside the baby's head and by using infrared absorption for directly measuring the blood oxygenation degree of the baby. Hence, these sensors include a radiation source and a detector, such that the radiation travels through the tissue of a baby's head. However, the pulse oximetry measurement relates to a device and a method highly sensitive to artifacts. Thus, the working conditions for pulse oximetry during parturition are highly unfavourable due to movements of both the baby and the parturient. Therefore, the genuine applicability of a pulse oximeter device in childbirth is highly questionable. The cited publications do not deal with this problem at all, but primarily these cited publications describe means for immobilizing this sensor assembly and for holding it against the head of a presently delivered baby. The publication EP-0,135,840 discloses both a simple flat-shaped sensor, hopefully holding on to a measuring site without special procedures, and a suction-pad resembling sensor attached to a child by the application of vacuum. The publication EP-0,575,737 discloses an elongated sensor, intended to be held at a measuring site by means of a folded spring element made of steel. In the publication EP-0,509,310, on the other hand, the intention is to hold an elongated sensor at a measuring site by means of an inflatable cushion in its extreme end, the purpose of said cushion, in its capacity as a thickening, being to prevent the sensor from slipping off from between the presently delivered child and the birth canal.

The publications EP-0,440,741 and WO-91/07910 describe sensors comprising both a pulse oximeter sensor and an EKG-sensor. The only means for the attachment of a sensor described in the publication EP-0,440,741 is a vacuum-operated suction pad assembly, while the publication WO-91/07910 discloses an inflatable cushion mounted on the extreme end of an elongated sensor, intended for preventing the sensor from slipping off from its position between the presently delivered baby and the birth canal.

On the other hand, the publication U.S. Pat. No. 4,197,853 describes a measuring sensor for measuring the partial pressures of oxygen and carbon dioxide through the skin of a patient, i.e. transcutaneously. The sensor of this publication includes in itself all detecting elements, in this case electrochemical cells. Such a transcutaneous measuring sensor is quite bulky and, as such, only applicable to the examination of a patient from outside the body, but it is not suitable for measuring the physical condition of e.g. a fetus or a presently delivered baby. As for this application, the sensor described in the cited publication is an element far too bulky and hard. Neither does the publication describe any means for its attachment to a measuring site or otherwise immobilizing it at a measuring site. Applying a measurement to an unrestrained and thus totally accessible patient by a transcutaneous procedure does not require any attachment means as the sensor can be simply pressed manually against the skin. Such application of a measurement to a fetus and a presently delivered baby is not possible.

BRIEF SUMMARY OF THE INVENTION

An object of the invention is to provide a measuring instrument that could be used for measuring or monitoring, for example, the physical condition of a presently delivered child. A particular object is to monitor the sufficiency of oxygen supply for a baby during parturition. A second object of the invention is such a measuring instrument which could be used for reliably measuring explicitly the condition of a presently delivered baby without the parturient affecting the measuring result through the measuring head. A third object of the invention is such a measuring instrument which provides a result affected as little as possible by movements of the presently delivered child and the mother. A fourth object of the invention is such a measuring instrument which has such a design that, under no circumstances, could it possibly be harmful either to the presently delivered child or the mother, and that it would interfere with the course of parturition as little as possible. A fifth object of the invention is such a measuring instrument which can be used for measuring the presently delivered child irrespective of the parturient and also, if necessary, the parturient irrespective of the presently delivered child. A sixth object of the invention is such a measuring instrument which, in general sense, can be used for measuring the physical condition of a single individual, such as a human being or an animal, irrespective of another individual, such as a human being or an animal, while these two individuals are in contact with each other. In particular, the meaning of this is that it must be possible to perform measurements over those sites or areas, at which the individuals are in contact with each other. A seventh object of the invention is such a measuring instrument which would remain as immobile as possible for example in the birth canal against the outermost cellular layer of a baby or, in the contact circumstances of other individuals, against any individual to be measured at a given time. An eighth object of the invention is such a measuring instrument which would be easy to use, easy to sterilize and to maintain sterilized. A ninth object of the invention is a measuring instrument which, if necessary, could be designed and manufactured to measure an object for single concentrations of various component media or for concentrations of a plurality of various component media.

The above drawbacks can be eliminated and the above-defined objects can be achieved by means of a measuring head of the invention, and by means of a method of the invention, which is characterized by what is set forth in the claims.

The most important benefit offered by the invention is that the inventive measuring head can be used for measuring and monitoring the physical condition of a presently delivered baby through the baby's skin without having to attach essentially anything to the baby. A second benefit offered by the measuring head of the invention is that it remains very reliably immobilized in the birth canal between the child and a wall of the birth canal and that, nevertheless, the measuring head can be positioned by a physician or a nurse in a site appropriate in terms of the measurement and progress of parturition. A third benefit offered by the measuring head of the invention is that it can be used for reliably measuring the condition of a baby without the mother's body, i.e. the birth canal wall, having any essential effect on the measuring result. A fourth benefit offered by the measuring head of the invention is that the device is highly insensitive to the movements of an object of measurement and, thus, despite the movements of a baby or a parturient, the measuring head is capable of producing a reliable measuring result. A fifth benefit offered by the measuring head of the invention is that various embodiments of the device can be used for measuring at least the carbon dioxide concentration and/or oxygen concentration from an object of measurement, and possibly other concentrations as well by appropriately selecting materials and/or detecting elements for the measuring head. A still further benefit of the invention is that the inventive measuring head can be used for measuring and monitoring other objects as well, such as human beings and animals in a mutual contact situation.

BRIEF DESCRIPTION OF THE SEVERAL VIEWS OF THE DRAWING

The invention will now be described in more detail with reference made to the accompanying drawings.

DETAILED DESCRIPTION OF THE INVENTION

Figure 1:
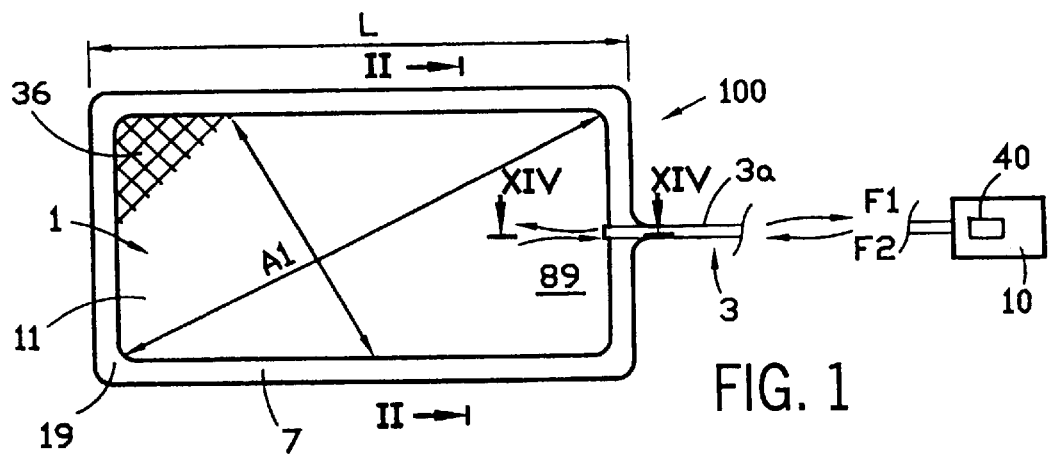
FIG. 1 shows a measuring head of the invention in a first embodiment in an external view from a direction I in FIG. 2.

The invention is based on a novel type of tonometric measuring head 100 which is asymmetric, regarding particularly the permeability to a gas to be analyzed. Accordingly, the tonometric measuring head of the invention is permeable to a subsequently analyzed gas from one side 8a thereof and is impermeable to this subsequently analyzed gas from its opposite side 8b. In addition, this novel asymmetric tonometric measuring head is generally flat or thin in the direction perpendicular to these two permeable and impermeable opposite sides 8a, 8b to the extent necessitated by properly placing the measuring head at a measuring site. This tonometric measuring head contains between such above-mentioned opposite sides or surfaces a measuring medium 20 for receiving a gas, the concentration of a, subsequently analyzed gas which is the object of measurement being ascertained by analyzing the measuring medium 20 contained in the measuring head 100 for its composition at least in terms of a gas component of interest. This is followed by conducting, if necessary, predetermined and predefined calculations for discovering the concentration in an object of measurement X1 or X1 and X2 which corresponds to the concentration obtained from the measuring medium 20. This way, an individual being examined reveals non-invasively through the individual's outermost tissue layer a gas component concentration existing in said individual at any given time, on the basis of which it is possible to draw conclusions regarding the physical condition of the individual, such as oxygen supply. For this purpose, the measuring head side 8a of the invention, which is substantially permeable to a subsequently analyzed gas, is placed on an individual X1 in contact with an outermost tissue layer, such as the skin, a mucosa, or some other appropriately chosen, accessible outermost tissue layer, the gas to be analyzed from the individual diffusing through these permeable surfaces into the subsequently analyzed measuring medium 20 present within the measuring head, from which the concentration of this gas or gas component is measured by means of an appropriate measuring method. On the other hand, the essentially impermeable side 8b in a measuring head of the invention settles towards the other individual or in contact with a second individual X2, this other individual not being able to diffuse any gas or the like into a subsequently analyzed measuring medium present within the measuring head. Thus, it should be appreciated that neither this other individual X2 nor any other environment over on the same side will be able to affect the measuring result. Furthermore, the novel tonometric measuring head 100 of the invention is substantially flexible as a whole so as to conform as well as possible to surface formations in the outermost tissue layer of an individual being examined.

This tonometric measuring head 100 of the invention comprises a substantially sealed chamber 1, having a wall 7 provided with divergent sides 8a and 8b, mainly consisting of flexible membrane materials. At least one of these membrane materials is permeable to a subsequently analyzed gas G1, G2 and, in certain embodiments provided with a second chamber 2, to a subsequently analyzed gas G3, G4, but impermeable at least to solid materials and liquids, regarding particularly a flexible first membrane material 11 or, respectively, a flexible fourth membrane material 14. This gas or these gases G1–G4, which the membrane material 11, 14 is permeable to, are generally constituted by carbon dioxide or oxygen, but may comprise something else as well, such as water in a gaseous form or carbon monoxide etc. Typically, each single permeable membrane material 11, 13, 14, 15 is highly permeable to just one gas, which is a preferred solution according to present thinking. If it is desirable to have a number of gases effectively diffusing into a measuring medium, the wall 7 of the chamber 1 is adapted to consist of adjoining sections of membrane material, such as strips of membrane material, each being highly permeable to at least one of the gases to be analyzed. There is no reason not to make a section of the chamber wall 7 from such a membrane material which is permeable to two or more gases to be analyzed. Hypothetically, it is appropriate to employ such permeable membrane materials 11, 13, 14, 15 which are not, at least not, highly permeable for example to gases detrimental to measuring, since this way it is simpler and likelier to provide a concentration measurement of the measuring medium 20 that is accurate and reliable. The fact that these permeable membrane materials let through such gas components which do not interfere with the concentration measurement of gases to be analyzed, is perfectly acceptable. However, the permeable membrane materials 11, 13, 14, 15 must be as strictly impermeable as possible to all other substances, such as liquids, solutions, salts dissolved therein, and solid materials.

In addition to this and according to the invention, said wall 7 of the chamber 1 and, respectively, the chamber 2 is partially constituted by a flexible second membrane material 12, which is impermeable both to a subsequently analyzed gas and at least to solid materials and liquids. In general, it is appropriate to make the second membrane material as poorly permeable as possible to materials possibly existing in or around an object of measurement. Thus, the wall/walls 7 of the sealed chamber 1, 2 consists/consist of membrane materials not permeable to harmful media, in other words, to solid materials and liquid materials as well as salts. However, the wall consists partially of at least one membrane material 11 or 14 permeable to a subsequently analyzed gas, and partially of a second membrane material 12 not permeable even to that material, i.e. gas. The first membrane material 11 and/or the fourth membrane material 14, on the one hand, and the second membrane material 12, on the other hand, constitute the divergent, generally essentially oppositely facing sides 8a and 8b for the wall 7 and, hence, for the chamber 1.

In addition to this, the tonometric measuring head contains the measuring medium 20 in the chamber 1, 2 within an internal cavity 9 constituted by the chamber wall 7. Thus, it is conceivable that the gas to be measured diffuses from a monitored individual through the first membrane material 11 or, for example, through the fourth membrane material 14 into the measuring medium 20 present within the chamber. The measuring medium 20 may comprise some pure gas, such as nitrogen or a noble gas, or a suitable gas mixture, such as air, or optionally some gel, such as a water-based gel, or optionally some pure liquid, liquid composition or salt solution, all referred to as liquids in this text. The measuring medium must be of a type capable of receiving a subsequently analyzed gas. In the case of a gel and a liquid, this means that the subsequently analyzed gas must be at least to some extent soluble in the measuring medium 20. The flat shape of the measuring head 100 is probably easier to maintain by using a measuring medium in the form of a gel and a liquid than by means of a gaseous measuring medium. However, the gas to be analyzed is always able to transfer into a gaseous measuring medium and, thus, at the moment, it is considered preferable to employ a gaseous measuring medium.

Moreover, this tonometric measuring head 100 comprises at least one guide means 3, extending between the chamber 1 and an external device 10. In case the measuring head includes another chamber 2, said measuring head is provided with at least one second guide means 5, extending between the chamber 2 and the external device 10. This single guide means 3, 5 or, as explained hereinafter, these several guide means 3, 5 is or are used either for carrying the measuring medium 20 between the cavity 9 and the external device 10 or for supplying the external device 10 with a measuring result obtained from analyzing the measuring medium 20 in the cavity 9. In its alternative embodiments, the measuring head 100 further includes a second guide means 4, 6. Each guide means 3, 4, 5, 6 and the chamber wall 7 are tightly joined together for a seal which does not allow any harmful substances through into the measuring medium 20 from a monitored individual X1, from another individual X2 or from the environment. It is obvious that the guide means 3, 4, 5, 6 and particularly its sheath are made from a material, which is also impermeable to substances having a harmful effect in the measuring medium 20 or to materials having a detrimental effect on information carried along the guide means.

Figure 8:
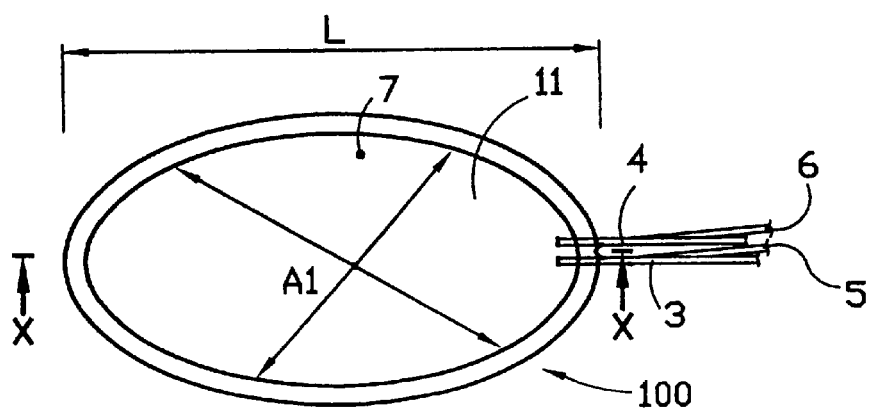
FIG. 8 shows a measuring head of the invention in a fourth embodiment in a side view from a direction VIII in FIG. 10.
Figure 10:
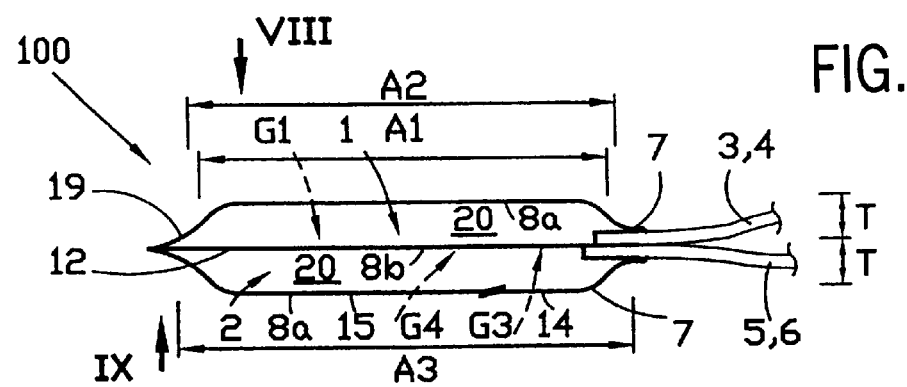
FIG. 10 shows the measuring heads of FIGS. 8 and 9 in a longitudinal section along a depicted plane X—X.

At first, reference is made to simple embodiments of the invention, which are only provided with a single chamber 1 and with a single membrane material permeable to a subsequently analyzed gas G1. The embodiment shown in FIGS. 1–2 includes one such chamber. Thus, the above-described continuous wall 7 for a tonometric measuring head of the invention is constituted by at least two areas, the wall including a first area A1 of said first membrane material 11 and a second area A2 of said second membrane material 12. These areas A1 and A2 of the wall 7 are parts of, and in a way parallel to the surface of the wall 7 and positioned on the diametrically opposite sides 8a and respectively 8b of the chamber. Consequently, the first area included in one side 8a settles exclusively against the outermost tissue layer of the body of a single monitored individual X1 and the second area A2 places itself against the outermost tissue layer of a second individual X2 who is in contact with the first individual X1. After all, when two individuals X1 and X2 are in contact with each other, the outermost tissue layers of these individuals are at least partially in contact and consequently against each other, the tonometric measuring head 100 of the invention placing itself between these individuals and separating them from each other. Respectively, the opposite sides 8a and 8b of the measuring head settle against each individual X1 and X2. Since the first area A1 was constituted by the membrane material 11 permeable to a subsequently analyzed gas and the second area A2 was constituted by the second membrane material 12 impermeable to said gas, it is conceivable that the diffusion of a subsequently analyzed gas from the first individual X1 is possible, but not from the second individual X2. FIGS. 8 and 10 illustrate an embodiment, in which one of the chambers is of the same type with the difference that the side 8b of this first chamber 1, and hence the second area A2, does not settle directly against the second individual X2, but indirectly against said second individual, since the second membrane material constituting this second side build forms a wall relative to the second chamber 2, the outer side 8a of said second chamber being provided with a third area A3 which settles against this second individual. Structurally, the embodiment of FIGS. 8 and 10 includes a chamber 1 which is of the same type as the chamber 1 in the embodiment of FIGS. 1–2. In other respects, this twin-chambered measuring head will be described in detail hereinafter.

A variety of tonometric measuring heads furnished with a single sealed chamber 1 are depicted in FIGS. 1–4. These single-chambered measuring heads 100 are both externally asymmetrical, i.e. the first membrane material 11 and the second membrane material 12 constitute the external surfaces for the measuring head, and internally, or functionally, asymmetrical. Thus, in reference to the embodiments of FIGS. 1, 2 and 3, 4, the measuring chamber 1 can be provided with a suitable subsequently described measuring system for measuring the concentration of just a single diffusing gas G1 in the case that the first membrane material 11 is effectively permeable to just one subsequently analyzed gas, but also with another type of measuring system for measuring the concentration of even several diffusing gases.

Figure 5:
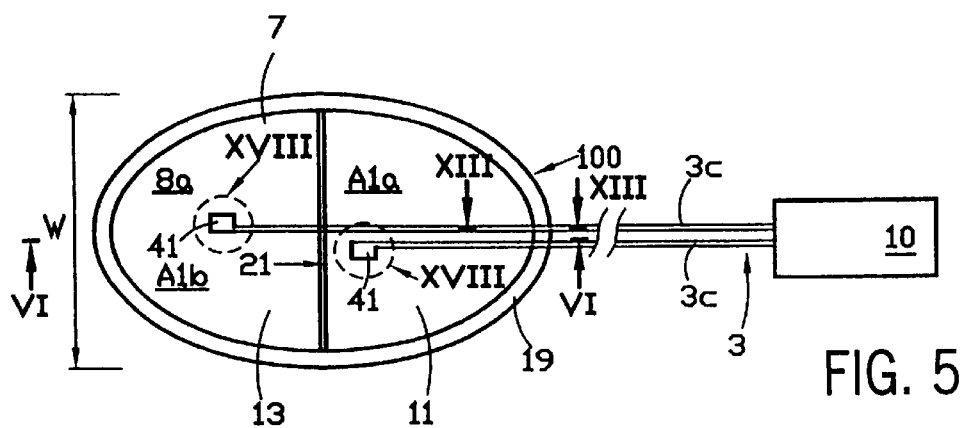
FIG. 5 shows a measuring head of the invention in a third embodiment in a plan view from a direction V in FIG. 6.
Figure 6:
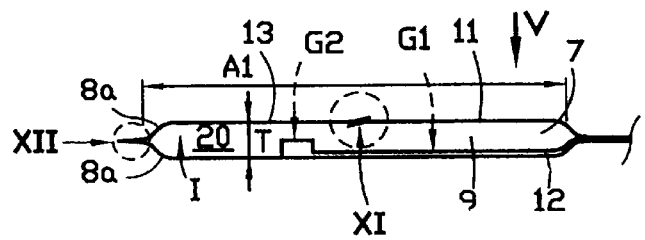
FIG. 6 shows the measuring head of FIG. 5 in a longitudinal section along a depicted plane VI—VI.
Figure 7:
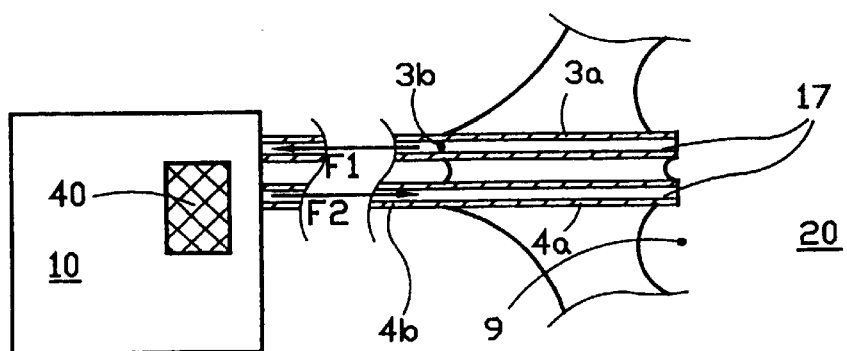
FIG. 7 shows a detail of the attachment of guide elements to a measuring head from a circle VII in FIG. 3, but in a larger scale.
Figure 9:
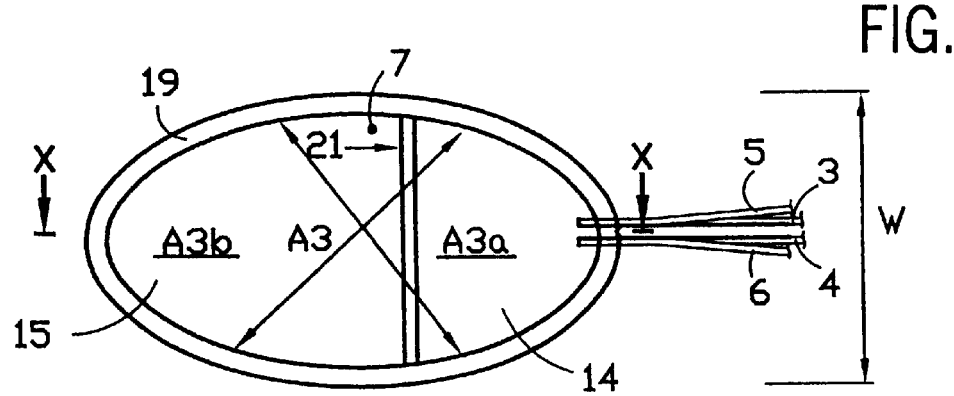
FIG. 9 shows the measuring head of FIG. 8 from the opposite side thereof in a view from a direction IX in FIG. 10.

FIGS. 5–6 illustrate a slightly further developed embodiment wherein the wall 7 of the chamber 1 has a first area A1 which is designed to include two sub-sections A1a and A1b, the first sub-section A1a being constituted by the above-mentioned first membrane material 11 and the second sub-section A1b being constituted by a third membrane material 13. In this type of embodiment, the first membrane material 11 is highly permeable to essentially one subsequently analyzed gas G1 and the third membrane material 13 is highly permeable to a second gas G2 to be analyzed. Both these membrane materials are of course impermeable to solid substances, dissolved salts, and liquids in order to avoid the diffusion of harmful substances, as described above. The first membrane material 11 and the third membrane material 13 are typically placed as extensions of each other to constitute one side 8a for the wall 7 of the chamber 1. It is also possible to have therebetween some other section, such as a joint 21, but even in that case these two membrane materials 11 and 13 effectively permeable to various gases G1, G2 are in any event included in the wall side 8a and especially the sub-sections A1a and A1b build together (i.e. A1=A1a+A1b) a first area A1, which is included in said side 8a. The second membrane material 12 constitutes an area A2 in the second side 8b of the chamber wall. The embodiment of FIGS. 9 and 10 is provided with a second chamber 2 which complies structurally with the above-described one, with the difference that the side 8b of this second chamber 2, and thus the second area A2, does not settle directly against the first individual X1, but indirectly against the first individual, since the second membrane material constituting this second side 8a forms a wall relative to the first chamber 1, the outer side 8a of said first chamber having its first area A1 settling against this first individual. Structurally, the embodiment of FIGS. 9 and 10 is provided with a second chamber 2 which is of the same type as the first chamber 1 in the embodiment of FIGS. 5–6. Otherwise, this twin-chambered measuring head will be described in detail hereinafter.

Such a composition of the wall area A1 and A3 to consist of two sub-sections A1a and A1b and respectively A3a and A3b, each comprising its own type of flexible membrane material, is a simple way of building a measuring head chamber 1 or 2, capable of measuring at least two subsequently analyzed gas components. In the chamber 2 of FIGS. 9 and 10, these two membrane materials 14 and 15 highly permeable to various gases are in any event included in the side 8a of the wall of said chamber, and particularly the sections A3a and A3b thereof constitute together (i.e. A3=A3a+A3b) a third area A3, which is included in said side 8a. It is of course possible to compose these wall areas A1 and A3 so as to comprise one such material which is permeable to two or more gas components to be analyzed. Hence, the invention relates also to such tonometric measuring heads, wherein the first area A1 and/or the third area A3 are composed of a material highly permeable to at least two subsequently analyzed gases or of a material possibly permeable to a larger number of subsequently analyzed gases. In this case, as mentioned in the preceding sentence, this area A1, A3 is consequently constituted by just one sub-section, comprising said above type of material, but, of course, this permeable material itself may be constructed e.g. as a laminate or otherwise inhomogeneous material for providing desired gas permeability characteristics.

FIGS. 8–10 illustrate a tonometric measuring head 100 of the invention provided with two chambers, a first chamber 1 and a second chamber 2, each operating separately from and independently of the other the same way as the above-described measuring head chamber 1. Relative to said first chamber 1 and starting from its second membrane material 12 or the side 8b, this second chamber 2 is positioned on the side of this second membrane material opposite to the first chamber 1. Consequently, the second membrane material 12 forms a partition between the first chamber and the second chamber 2, as seen from FIG. 10. This second chamber of the measuring head contains some measuring medium 20 as well, and this second chamber 2 is connected with at least one second guide means 5, which is in communication with the above-mentioned external device 10 exactly the same way as the first chamber 1. This second chamber has a wall 7 which comprises at least said second membrane material 12, which is impermeable both to a subsequently analyzed gas and to at least solid substances, dissolved salts, and liquids. In addition, this second chamber wall 7 includes a third measuring head area A3, which is a part of, and in a way parallel to the wall surface and is constituted by a fourth membrane material 14 permeable to a subsequently analyzed gas but impermeable to liquids and solids. The second chamber 2 is provided with a third area A3 of the wall surface, which is opposite to the second area A2 constituted by the second membrane material, and this third area A3 is constituted by said fourth membrane material 14, which is highly permeable at least to a gas G3 to be analyzed. This second measuring chamber 2, along with its measuring medium 20, operates in a fashion similar to the single chamber 1 of the above-described measuring head. In other words, the subsequently analyzed gas diffuses through the outermost tissue layer of a monitored individual X1 or X2 into the measuring medium 20 through the fourth membrane material 14 of the third area A3 of the second chamber placed against said tissue layer. This measuring medium 20 is analyzed for the concentration of a subsequently studied gas and calculations are used for determining its concentration in the object of measurement. The first measuring chamber 1 of FIGS. 8–9 functions exactly as described above and is structurally exactly as explained above. Thus, in the embodiment shown in these figures, the measuring head of the invention is capable of measuring both individuals X1 and X2, who are in contact with each other, independently of each other and without disturbing one another either for the concentration of one and the same gas or for the concentration or various concentrations of different gases.

In the embodiment of FIGS. 8–10, the wall 7 of the first chamber 1 includes a first section A1 which is constituted by just one first membrane material 11. In this embodiment, the wall of the second chamber 2 has its area A3 partially constituted by a fourth membrane material 14, which is highly permeable to one subsequently analyzed or a third gas G3, and furthermore, the third area A3 is partially constituted by a fifth membrane material 15, which is highly permeable to a fourth subsequently analyzed gas G4. Thus, in this case, the second chamber 2 can be used for measuring for example concentrations of the third subsequently ana- lyzed gas G3 and the fourth subsequently analyzed gas G4. In the case of two measuring chambers, both chambers 1 and 2 can be adapted to measure just one subsequently analyzed gas, the first area A1 and the third area A3 of said chambers typically comprising just one type of first and fourth membrane material 11 and 14, respectively. In fact, the figures illustrate an embodiment, wherein the wall of the first chamber 1 has a first area A1 which only comprises a first membrane material 11 and the second chamber 2 has a third area A3 which comprises a fourth and fifth membrane material 14 and 15. In addition, the first area of the first chamber 1 can be composed to comprise two membrane materials 11 and 13 highly permeable to two different gases.

Figure 2:
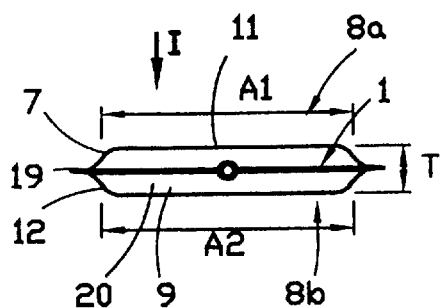
FIG. 2 shows the measuring head of FIG. 1 in a cross-section along a depicted plane II—II.
Figure 3:
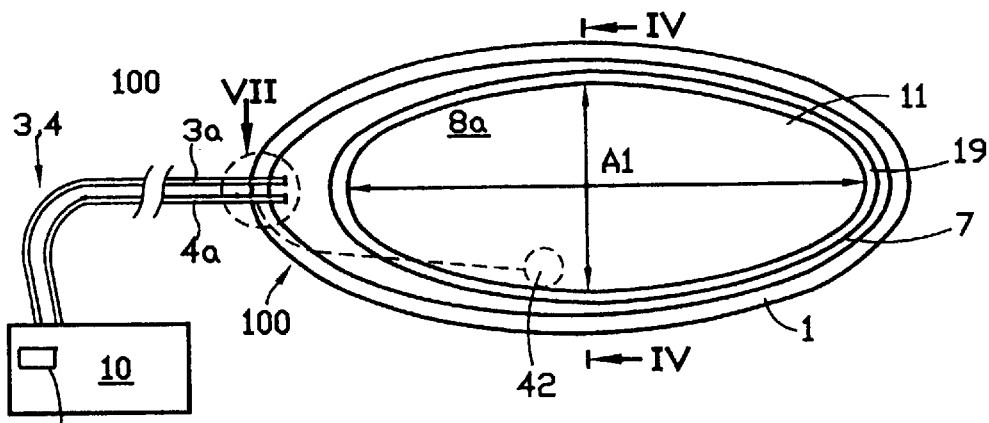
FIG. 3 shows a measuring head of the invention in a second embodiment in a plan view from a direction III in FIG. 4.
Figure 4:
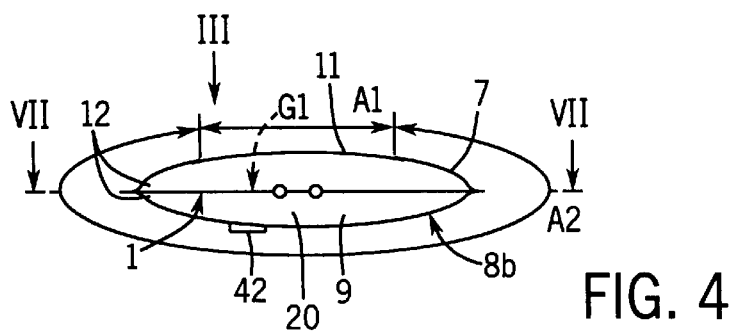
FIG. 4 shows the measuring head of FIG. 3 in a cross-section along a depicted plane IV—IV.

The wall 7 is provided with a first area A1 and a second area A2, which together, or added together, constitute the entire surface area A1+A2 for the wall of the chamber 1. Said second area A2 constitutes at least 40% and typically at least 50% of this entire wall area A1+A2 of the chamber. However, the second area A2, composed of an impermeable second membrane material, constitutes no more than 80% and typically no more than 70% of the entire wall area A1+A2 of the chamber. FIGS. 1 and 2 illustrate an embodiment, wherein the second area A2 constitutes roughly 45% of the entire surface area A1+A2 of the chamber. In this instance, this is implemented in such a way that the first membrane material 11 has a length and/or a width which fall slightly short of the length and/or the width of the second membrane material 12, when measured all the way to a joint edge 19 between the first and second membrane materials. In FIG. 1, this is not clearly visible but in FIG. 2 it is perceivable from the fact that the section shown in the figure to be above the joint edge 19 (=area A1) has a slightly lower height in a vertical direction normal to the joint edge, this membrane area having a surface area which is also smaller than the area (=area A2) extending downward therefrom and, hence, the surface area. FIGS. 5 and 6 illustrate an embodiment, wherein the second area A2 is roughly equal in size to the first area, said second area A2 constituting roughly 50% of the surface area A1+A2 of the entire wall. FIGS. 3 and 4 illustrate an embodiment, wherein the second area A2 constitutes 70–80% of the entire surface area A1+A2 of a wall, said second area A2 extending into the area of a first side 8a, as perceivable from the figures. This embodiment is very effective in terms of protecting the measuring medium 20 from the effects of a second individual X2 and the environment. In principle, it is possible to further increase the size of an area A2 while the proportional surface area of an area A1 is dwindling, but in this case, the surface area, whereby the subsequently analyzed gas diffuses through a first, and possibly a third, fourth and fifth membrane material, diminishes often too much, whereby the response to a change of the object of measurement becomes slower and, thus, the measuring accuracy may be impaired. Depending on an object of measurement, however, even this type of embodiment may sometimes be useful. These above-defined threshold values apply also to the embodiment shown in FIGS. 8–10 and provided with two chambers 1 and 2. Thus, the wall 7 of the first chamber 1 has a surface area which comprises a first area A1, constituted by a permeable membrane material 11 of the first chamber, and a second area A2, constituted by a second membrane material 12, the wall of said first chamber having a surface area A1+A2, exactly as described above. The wall 7 of the second chamber 2 has a surface area which comprises an impermeable second membrane material 12 and a fourth and fifth membrane material 14 and 15, which are permeable to gases and constitute a third area A3 providing a section permeable to gases. Thus, the entire surface area A2+A3 of the second chamber is constituted by the second section and the third section together. Hence, the second area A2 constitutes a part of each chamber and it is counted twice, first as one area of the first chamber and then as one area of the second chamber. In the embodiment of FIGS. 5–6, the first permeable area A1 is constituted by a section of two permeable membrane materials, i.e. by the first membrane material 11 and the third membrane material 13, which together make up this first area. Respectively, in the embodiment of FIGS. 8–10, the third permeable area A3 is constituted by a section of two permeable membrane materials, i.e. by the fourth membrane material 14 and the fifth membrane material 13, which together make up this third area The first and third, as well as the fourth and fifth membrane material 11, 13 and 14, 15, highly and expediently permeable to the gas G1, G2, G3 or G4 to be analyzed, are each generally composed of a single type of material or usually of a single type of plastics, at least according to current knowledge. Of course, it is possible to discover that some applications, i.e. for effective transmission of a given gas, can be carried out with a suitable material composition or laminate. The impermeable second membrane material 12 is constituted either by a single type of material or, alternatively, by a laminate consisting of membranes of various materials. It is especially this last-mentioned laminate option that is capable of rendering the second area A2, constituted by the second membrane material 12, extremely impermeable to all surrounding substances while still maintaining the second membrane material 12 thin in terms of its total thickness. Of course, it is a principal consideration in the selection of a material for the first, third, fourth and fifth membrane material 11, 13, 14, 15 that the membrane material be as highly permeable as possible at least to a desired, subsequently analyzed gas, but as poorly permeable as possible to other solid or liquid substances, including dissolved salts.

In addition to the above, it is an objective to provide a measuring head of the invention, within the recognized limits, with such membrane materials 11–15, having an elasticity which is as low as possible, i.e. a modulus of elasticity which is as high as possible. An effort should be made to avoid highly elastomer types of membrane materials as those stretch in the direction of a membrane surface and swell elastically due to the pressure of a fluid or a gas present in the chamber 1, 2. However, this does not preclude the use of an elastomeric material in a measuring head of the invention as the gas-permeable membrane material 11, 13–15, especially if the impermeable second membrane material 12 is clearly a non-elastomer. Thus, this second area A2 constituted by the non-elastic membrane material 12 keeps the entire measuring head in a sufficiently proper shape. It is possible to employ elastomeric permeable membrane materials especially in the embodiment of FIGS. 3–4, wherein the second area A2 covers more than 50% of the entire measuring head area. Also the embodiments of FIGS. 5–6 and 9–10 allow readily the use of an elastomeric material at least as one of the permeable membrane materials 11 or 13 or 14 or 15. This high modulus of elasticity or sort of "hardness" of membrane materials is used for eliminating an elastic expansion of the chamber wall 7 of a measuring head and generally any kind of elongation as effectively as possible. Since, according to the invention, the measuring head 100 must nevertheless be pliable or be composed of a pliable membrane material, such a pliability is achieved by using the materials in the form of very thin membranes. Thus, indeed, the membrane materials constituting the walls of the measuring chamber 1, 2 do not undergo dimensional changes in the direction of the surface of the chamber wall 7, but the membrane materials are readily pliable in a direction normal to the surface of the wall 7, i.e. assume a curved shape. Consequently, the measuring head can be maintained in a flat or plate-like shape during the use without an essential tendency to swelling, while managing to keep the measuring head as pliable or flexible as possible. For this purpose, all said membrane materials 11–15 have a thickness S which is no more than 0.2 mm, and preferably no more than 0.1 mm, and typically no more than 0.05 mm. In order to achieve a sufficient gas permeability for the first, third, fourth and fifth membrane material, it is generally appropriate to provide those with a slightly less thickness, i.e. no more than 0.1 mm, preferably no more than 0.05 mm, and typically within the range of 0.03–0.01 mm. Thus, the second membrane material 12 may be slightly thicker. With such membrane material thicknesses, the chamber 1 or the chambers 1 and 2 of a measuring head of the invention, and subsequently the entire measuring head, can be made pliable and the membrane materials permeable to a subsequently analyzed gas can be provided with a high permeability. The impact of a possible elasticity of a membrane material on the shape of a measuring head can be limited by laminating such a membrane material, for example on the side of its cavity, a mesh 36 of a suitable material, a part of which is schematically shown in FIG. 1. Being non-elastic, yet pliable, said mesh prevents the elongation of an elastomeric membrane material. Other means for managing the shape of a measuring head will be described hereinbelow.

Figure 11A:
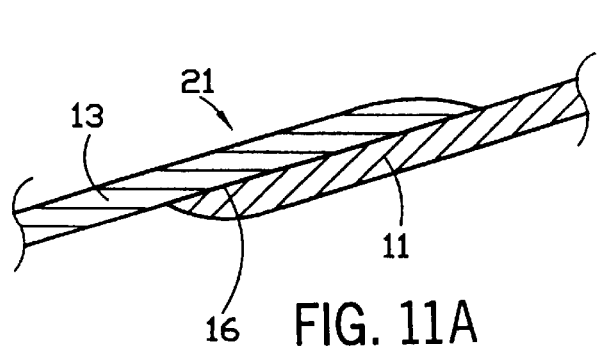
FIGS. 11A and 11B show a joint between two different materials in the wall of a measuring head of the invention from a circle XI in FIG. 6, but in a larger scale.
Figure 11B:
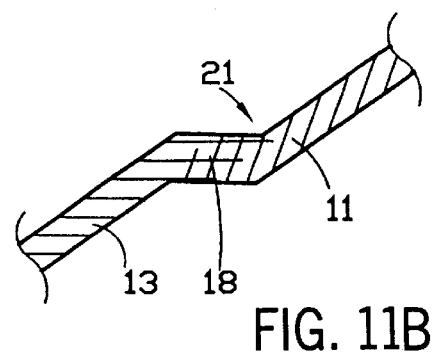
Figure 12A:
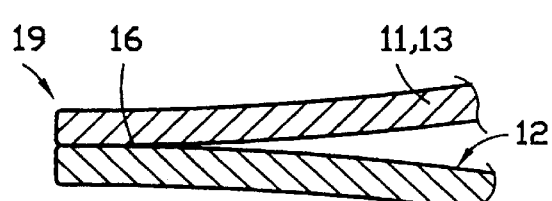
FIGS. 12A–12C show a joint between a permeable and an impermeable wall material in a measuring head of the invention in a cross-section from a circle XII in FIG. 6, but in a larger scale.
Figure 12B:
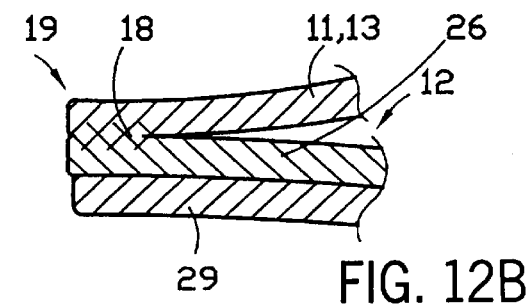
Figure 12C:
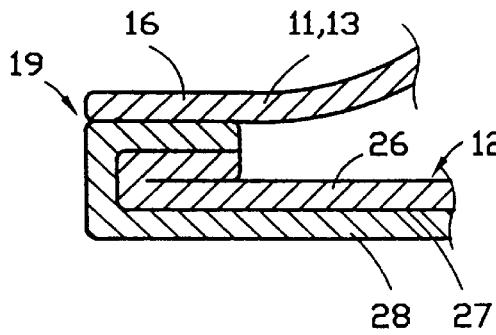
Figure 13:
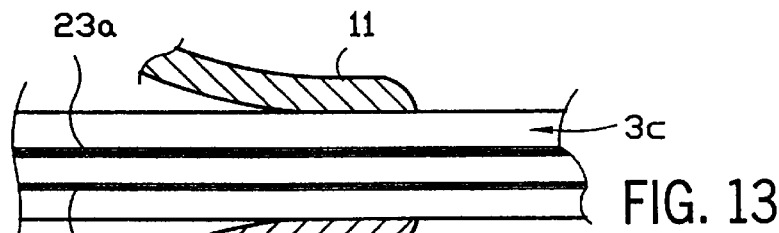
FIG. 13 shows types of guide means alternative to FIG. 7 in a longitudinal section along a plane XIII—XIII in FIG. 5.
Figure 14:
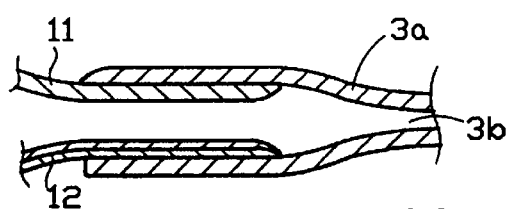
FIG. 14 shows joints for guide means alternative to FIG. 7 in a longitudinal section along a plane XIV—XIV in FIG. 1.

In the event that the first area A1 or the third area A3 of a wall is constituted by two gas-permeable or first and third membrane materials 11, 13, it is necessary to have a tight joint 21 therebetween. The tight joint can be made by joining the membrane materials, which are extensions of each other in the wall 7, together by means of an adhesive 16, as shown in FIG. 11A, or those can be welded together by a fusion joint 18, as shown in FIG. 11B. This fusion joint can be made either by hot sealing or ultrasound welding. It is exactly the same way that the permeable membrane materials 11, 13 or of course the membrane materials 14 and 15, respectively, can be attached to the second membrane material 12 either by means of an adhesive 16, as shown in FIGS. 12A and 12C, or by a welded fusion joint 18, as shown in FIG. 12B. The permeable membrane materials 11, 13–15 are attached to each other by means of a joint 19, which can be an edge joint 19 as shown in FIGS. 1–2, 5–6 and 8–10 or a joint 19 spaced from the edge of a measuring head in the direction of the surface of the wall 7, as shown in FIGS. 3–4.

These FIGS. 12A–12C also disclose a variety of alternative structures for the second membrane material 12. In FIG. 12A, the second membrane material 12 consists of a membrane section made in a single type of plastics. In FIG. 12B, the second membrane material 12 comprises a laminate of two different types of plastics 26 and 29, whereby one type of plastics 26 for this laminate can be selected to be beneficial e.g. in terms of a subsequently welded fusion joint 18 and the other type of plastics 29 merely in terms of its ability to eliminate diffusion in accordance with the invention. FIG. 12C depicts a laminate comprising three discrete layers, which is used as the second membrane material 12. In addition, the edge of this laminate is folded towards the interior of the chamber in order not to have the material constituting a middle layer 27 exposed outside the measuring head. This type of solution may be necessary, e.g. whenever some very designated material 27 is required for achieving a given and/or sufficiently effective elimination of diffusion, but this material is of a type which either does not withstand the conditions in an object of measurement or causes complications in a monitored individual or leads to measuring errors or other problems e.g. as a result of dissolution. In the embodiment of FIG. 12C, the second membrane material 12 has an outermost layer 28 of a type which is adapted to be compliant to sizing 16, while both inner layers 27 and 28 can be selected merely in terms of an ability to effectively eliminate diffusion or other permeability. In this case, for example the outermost and innermost layers 28, 26 may comprise different types of plastics and the middle laminate layer 27 may comprise a pliable foil of metal. At any rate, all junctions 16, 18, both between the permeable membrane materials 11, 13–15 and between the permeable membrane materials and the impermeable membrane material 12, are attached to each other by means of such a joint 19, 21 which does not develop rigid or hard spots in the measuring head. Neither does the measuring head of the invention include any sort of braces, but the measuring head 100 has an overall pliability which is substantially equal to the combined pliability of membrane materials constituting the measuring head chamber 1 and/or 2.

In this context, it should be noted that the high permeability of membrane materials to various gases and, respectively, the elimination of diffusion or the impermeability are relative values. No membrane material is permeable to any gas totally without resistance but lets through various gases in various amounts per unit time, depending on a discussed type of material and also on a pretreatment applied to the material. For example, the permeabilities to carbon dioxide and oxygen on ethylene-vinyl acetate copolymer are proportioned roughly as 7:1, on LDPE as well as polyurethane roughly as 5:1, and on silicone as well as polypropylene roughly as 3:1. Generally, as far as plastics are concerned, the permeability to carbon dioxide is higher than the permeability to oxygen. It is particularly important to make note of ionomers which have a very high permeability to oxygen and a minimal permeability to carbon dioxide. However, the numeral values may fluctuate considerably and change as materials are developed and, thus, the foregoing is not to be construed as limiting the scope of the invention. Consequently, it must be concluded that a membrane material of the invention, which is permeable to a subsequently analyzed gas, e.g. G1, is likely to be perceivably permeable to some other gas as well. However, with a difference in permeabilities between such gases, the concentration of a gas to be analyzed in the measuring medium 20 of the chamber increases more rapidly and in a shorter time to a stationary value than said other gas. After all, as described above, the membrane material has been selected to be as highly permeable as possible to a gas to be analyzed. If the discussed other gas is such that there is no need to know its concentration, it will suffice that detecting elements 40, 41 be designed and manufactured such that this other gas does not in any case lead to an excessive measuring error in the measurement of a gas component to be analyzed. The concentration of this more poorly diffusing other gas in the measuring medium can be reduced by continuously feeding through the measuring chamber a pure, i.e. not containing the relevant gases, measuring medium 20 at such a suitable volume flow rate that the concentration of a subsequently analyzed gas has time to increase to a concentration yielding a reliable measuring result, but the concentration of an interfering other gas component remains substantially low, i.e. relatively lower than the concentration of a gas to be analyzed. This contributes to the elimination of the effect of a disturbing gas and is readily implementable e.g. with the measuring heads of FIGS. 3–4 and 8–10, provided with two flow channels 3b, 4b. On the other hand, if the discussed other gas is such that its concentration needs to be known, there are a variety of possibilities. First of all, it is possible to use a measuring medium circulation F1, F2 proportioned to the permeability to a more poorly diffusing gas component, in other words, a slow circulation along tubes 3a, 4a, or to effect a measurement back and forth along the tube 3a, whereby the concentration of this gas as well within the measuring medium has time to increase to a reliable level. A similar condition is achieved in the embodiment of FIGS. 5–6, wherein the measuring medium 20 remains continuously in the chamber 1. Yet another possibility is to make the first membrane material 11 of a material highly permeable to a first gas GI and more poorly permeable to a second gas G2, and the third membrane material 13 of a material highly permeable to a second gas G2 and more poorly permeable to the first gas G1. This way, it is possible to provide both gas components G1 and G2 with an averagely common degree of permeability, especially by fine adjusting the differences in permeability to be averagely equal by selecting appropriately the surfaces areas of subsections A1a and A1b.

As for impermeable membrane materials, it should be noted that there is no single material that would be an extremely good and effective blocker of diffusion. However, the best impermeable membrane materials have a permeability which is in the order of 1/1000 relative to the poorest, perhaps necessary permeable membrane materials and in the order of just 1/100,000 relative to the best required permeable membrane materials. Using the above-described type of laminates as the impermeable second membrane material 12, it is possible to provide those with a permeability which is in the order of 1/106, especially by using a foil metal as one of the layers.

The guide means mentioned in the beginning comprise a tube 3a including at least one flow channel 3b, said tube having a jacket 17 constituted by a material substantially impermeable to gases, liquids, and solids. The channel 3b of this tube 3a is at one end thereof in a flow communication with a cavity 9 and at the other end with detecting elements 40 included in the external device 10. This type of simplest embodiment is shown in FIGS. 1–2. In this case, the measuring medium 20 is carried at preset intervals or, if necessary, along the tube flow channel 3b as a flow F1 from the chamber 1 to the detecting elements 40 of the external device for analyzing the measuring medium 20 for the concentration of a desired gas component or for the concentration of desired gas components. This analysis is followed by returning the measuring medium 20 as a flow F2 along this very same flow channel 3b into the first chamber 1. Optionally, in addition to the above-mentioned first tube 3a, between the measuring chamber and the external device 10 can be fitted a second guide means 4 constituted by a second tube 4a, said tube being also provided with a jacket 17 constituted by a material impermeable to gases, liquids, and solids. This second tube 4a includes a channel 4b which is also in communication at one end thereof with the cavity 9 and at the other end with the detecting elements 10. Thus, the measuring medium 20 from the cavity 9 of the chamber 1 is circulated e.g. along the first flow channel 3b as a flow F1 to the detecting elements 40 of the external device, and thence further along the second tube channel 4b as a flow F2 back into the cavity 9 of the chamber 1. Since, in this case, the supply channel to the detecting elements 40 and the return channel from the detecting elements to the chamber are separate from each other, the measurement and analysis can be performed, if necessary, as a continuous process, the flow channels 3b, 4b carrying a continuous flow. This type of embodiments are shown in FIGS. 3–4, 7 and 8–10. It is obvious that, in this case as well, the analysis can be performed sequentially, i.e. the circulation of the measuring medium 20 from the chamber through the detecting elements 40 can be effected periodically.

Figure 18A:
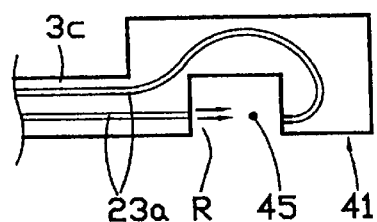
FIGS. 18A and 18B show sensor elements to be placed within a measuring head of the invention from circles XVIII in FIG. 5, but in a larger scale.
Figure 18B:
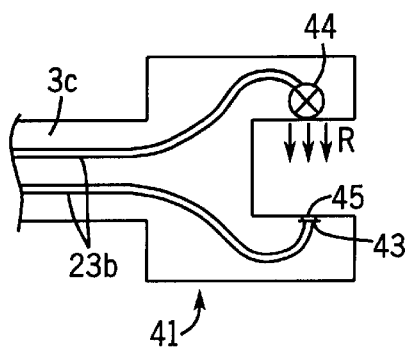

The foregoing description has dealt with an embodiment, wherein the detecting elements are included in an external device. It is also possible to include detecting elements 41 directly in the chamber 1 or 2, as shown in FIGS. 5–6. These detecting elements 41 may be constituted either by an intra-chamber radiation source 44 and a detector 43, and by a bandpass filter or bandpass filters possibly arranged therebetween. See FIGS. 18A, 18B. The radiation source 44 and the detector 43 are spaced from each other by a gap 45, the measuring medium present in the chamber spreading into the gap therebetween, whereby a radiation R is absorbed to emit a signal to electrical conductors 23b. It is obvious, of course, that an optical signal can be delivered inside the chamber 1 and 2 also by optical guides 23a, such as optical fibers, and the path thereof can be provided with a gap 45 for absorbing the radiation R therein. In this case, the radiation source and detectors as well as bandpass filters are included e.g. in an external device, even though the measuring gap 45 is inside the chamber. These embodiments of detecting elements 41 are depicted in FIGS. 18A, 18B. The detecting elements 40 included in the external device 10 are not structurally described, being of any appropriate type, since an external device does not impose such demands on size, power, etc. which must be met by the detecting elements 41 placed inside the chamber 1, 2. After all, being within the chamber, the detecting elements 41 must be as small as possible and also as pliable as possible. In this case, the chamber 1 does not have its cavity 9 linked with an external device by way of tubes, but e.g. by way of electrical guides 23b or optical guides 23a, said guide means 3 comprising an optical or electrical cable 3c. The detecting elements 40, 41 are capable of identifying and measuring the concentrations of various gas components by the application of any prior known or novel technology. The detecting elements are also capable of applying any methods or instruments for improving a resolution in the measurement of gas components.

Said single chamber 1 or said two chambers 1 and 2 together in a measuring head of the invention are flat and elongated in shape, i.e. have a baggy and braceless structure. This last-mentioned aspect is particularly point out, since the measuring head explicitly does not include any mentionable or sizable rigid or hard members. Most preferably, the measuring head 100 is completely without rigid members, but, in case it is absolutely necessary to include those, such members must be as flat as possible in the direction of a chamber thickness T and even otherwise as small as possible. Such small rigid members may be constituted by the detecting elements 41 and separate sensors 42. Thus, the measuring head of the invention is absolutely pliable to the shape of its application site, as described subsequently in more detail. In the measuring head, the chamber has a length L which is within the range of 2–20 cm, a width W which is within the range of 1–10 cm and, with this length and width, the measuring head may be rectangular in shape, as shown in FIG. 1, elongated with rounded ends, as shown in FIG. 3, or oblong like an ellipse, as shown in FIGS. 5 and 8–9. As predictable from these dimensional ranges, it is generally the most preferable option to make the measuring head 100 of the invention at least slightly elongated, the length L of its chamber exceeding its width W. Preferred ratios for the length L and the width W may include 1:2, 1:3 and 1:5, but it is possible to use such a long chamber that the ratio is 1:10. However, a very narrow and long chamber is not preferred for the reason that it twists easily at an application site, whereby its side 8a permeable to a subsequently analyzed gas may twist to an incorrect position and result in a measuring error. Thus, it is presumed that the most favourable ratios between length and width are found within the range of 1:1.5–1:5.

Figure 19:
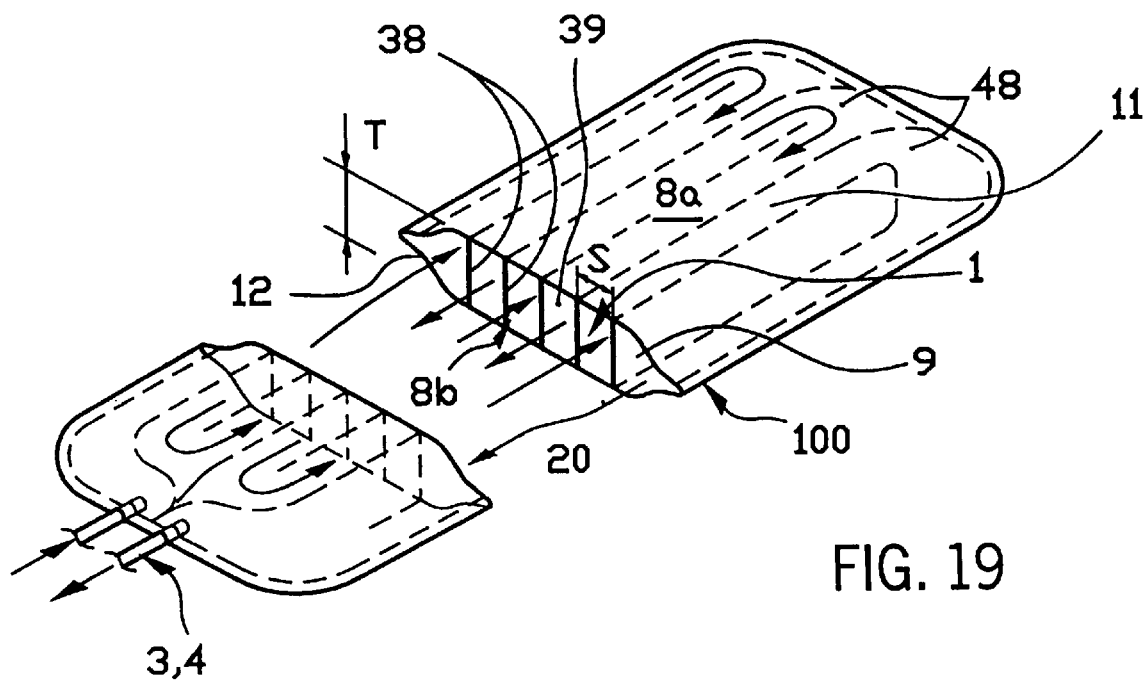
FIG. 19 shows a measuring head of the invention in a fifth embodiment, which enables a special flatness, partly in a cross-section and partly from outside in an axonometric view.
Figure 20:
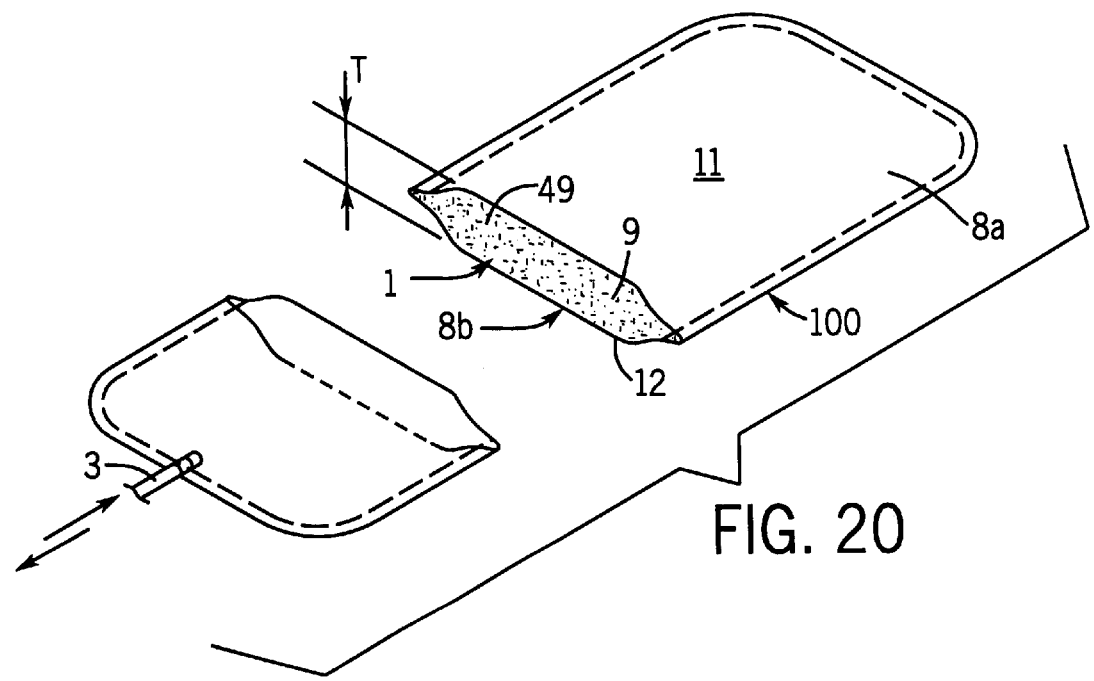
FIG. 20 shows a measuring head of the invention in a sixth embodiment, which enables a special flatness, partly in a cross-section and partly from outside in an axonometric view.

FIGS. 19 and 20 illustrate various ways of keeping a measuring head 100 of the invention in a desired flat shape as effectively as possible. FIG. 19 depicts a cavity 9 in a tonometric measuring head, which is provided with partitions 38, connecting the opposite and roughly parallel sides and extending crosswise or possibly perpendicularly thereto and made of some appropriate pliable material, perhaps the same membrane material as the rest of the chamber. There are a number of these partitions in one chamber 1, and of course in a possible second chamber 2 as well, separated from each other by spaces S parallel to the sides 8a, 8b of the chamber wall 7, resulting therebetween in a number of intra-chamber flow channels 39. The adjacent partitions 38 extend alternately to a sealed contact with the ends of a chamber and are alternately spaced by a small passage 48 from the chamber ends, as perceivable from FIG. 19, the number of flow channels constituting a single channel 39 extending back and forth in a zigzag pattern, along which the measuring medium 20 is able to make its way through the chamber. Thus, the measuring medium essentially fills the entire chamber and the diffusion of a gas to be analyzed through the first and third area A1, A3 occurs effectively. However, the partitions 38 tie the opposite chamber sides 8a and 8b to each other, preventing the same from drawing away from each other, even as a gas pressure P or a fluid volume or the like V present in the chamber is increased, and at the same time, said partitions reduce the collapsing of the chamber as a result of compression Q. The partitions can be welded or glued at the edges thereof securely to the inner surfaces of membrane materials 11, 12 facing the cavity 9, or the chamber can be manufactured from a prefabricated, pliable and flat tubing profile or some other way. In the embodiment of FIG. 20, the cavity 9 is filled with an open-cell spongy or foamy material or with a fiber-matting resembling elastic material 49, said material being in a secure contact with the inner surfaces of the opposite chamber sides 8a, 8b to prevent the same from drawing away from each other, even as a gas pressure P or a fluid volume or the like V present in the chamber is increased, and at the same time, said material reduces the collapsing of the chamber as a result of compression Q. Hypothetically, this latter solution is not favourable in the measuring heads of FIGS. 3–4 and 8–10 based on the circulation of a measuring medium, but it is indeed favourable in the measuring heads of FIGS. 1–2 and 5–6, wherein the measuring head, by virtue of the elasticity of the filling material 49, collapses for the time lapse that the measuring medium is exhausted for an analysis and resumes its original shape or condition as the measuring medium is returned. On the other hand, the former solution comprising said channels 39 is hypothetically preferable in the measuring heads of FIGS. 3–4 and 8–10, but not in the measuring heads of FIGS. 1–2 and 5–6.

The measuring medium 20 present within the cavity 9 in the chamber 1, 2 may comprise a gel, necessitating the use of intra-chamber disposed detecting elements 41 as depicted in FIGS. 5–6. The measuring medium may also comprise a fluid, whereby the measuring medium can be circulated along the tube 3a or tubes 3a and 4a through the detecting elements 40 of an external device or the measurement can be performed directly inside the chamber by means of the detecting elements 41. At the moment, it is presumed that the most favourable measuring medium 20 comprises a gas or a gas mixture, whereby the measurement can be performed by circulating the measuring medium 20 along the tube 3a or along the tubes 3a and 4a through the detecting elements 40 of an external device, or the analysis can be performed directly in the chamber 1 and 2 by means of the detecting elements 41 included therein. Depending on whether the permeable, pliable membrane materials are adapted to allow into the chamber 1 and 2 effectively one or more gases to be analyzed, said detecting elements 40, 41 are used to measure either a single analysis value or a plurality of analysis values, regarding the composition of the measuring medium present in the chamber and particularly the concentration of one or more predetermined gas components possibly contained in the composition.

Within the chamber 1, 2, the measuring medium 20 is adapted to have such a volume V or such a pressure P that the diametrically opposite areas A1–A2 or A2–A3, i.e. the opposite sides 8a and 8b, of the wall 7 of the chamber/chambers have an average spacing T which is no more than 5 mm, preferably no more than 2 mm, and typically in the order of 1 mm. This definition relates explicitly to the average spacing T between the opposite areas, which can be verified whenever the measuring head of the invention can be monitored in an unrestrained condition, in other words, not at a measuring site. At a measuring site, the measuring head has its opposite walls 8a and 8b subjected to a compressive force Q, having a strength which fluctuates at various points over the length L and the width W of the measuring head. Thus, at a measuring site, the opposite walls of the measuring head may have therebetween a spacing which is larger T' or smaller T", as can be seen from FIG. 16. It is generally preferable to set the volume V and the pressure P of the measuring medium 20 to be such that, at a measuring site, the smallest spacing T" is more than zero and, thus, the areas of the opposite sides 8a, 8b are not in contact with each other within the chamber cavity 9. However, there is nothing to stop the opposite walls from touching each other at some points, but this contact area must be very small compared to the surface of the entire first area A1. The reason for this is that the points, at which the opposite chamber sides 8a and 8b, i.e. the opposite areas A1 and A2 or A3 and A2, are in contact with each other, do not allow a required diffusion from the individual X1 to the measuring medium 20 at least in a considerable or substantial degree. At least the area, over which the chamber thickness dimension T" is zero, should be as small as possible, since otherwise the measuring head will be impaired in terms of its measuring sensitivity. In reference to FIGS. 19 and 20, the above description has dealt with other means for managing the shape of a measuring head of the invention and particularly for maintaining the measuring head in all conditions as uniformly as possible in a flat shape, as described above. Of course, the means shown in FIGS. 19 and 20 can also be applied for providing the measuring head with another kind of shape, if necessary.

According to the invention, the first membrane material 11 partially constituting the first area A1 of a chamber wall has its section A1a located, when perceived in relation to the guide means, at the proximal end of a measuring head and the third membrane material 13 partially constituting this first area has its section A1b located at the distal end of the measuring head. Respectively, the fourth membrane material 14 has its section A3b located, when perceived in relation to the guide means of a second chamber, at the proximal end of a measuring head and the fifth membrane material 15 has its section A3a located at the distal end of this second chamber. This means, of course, that the chamber has its guide means 3, 4, 5, 6 extending from the distal end thereof, when perceived in relation to an object of measurement C, D; X2, X1. In such an embodiment, especially if the measurement deals with carbon dioxide and oxygen, the first membrane material 11 is highly permeable to carbon dioxide and the third membrane material 13 is highly permeable to oxygen. Examples of possible membrane materials highly permeable to gases include: polystyrene, which is highly permeable to carbon dioxide and poorly to oxygen; polysiloxanes in general, amongst which there are polymers and copolymers permeable to various gases, as well as especially fluorosilicones and nitrile silicones, which are effectively permeable to carbon dioxide and oxygen, as well as silicone elastomers, which have an extremely high permeability to carbon dioxide and a good permeability to oxygen; polyethylene (PE), which has a reasonably good permeability to carbon dioxide and a poor permeability to oxygen and nitrogen; polypropylene (PP), which is highly permeable to carbon dioxide and poorly to oxygen and has no permeability to nitrogen; polybutadiene, which has a very good permeability to carbon dioxide and a moderate permeability to oxygen and nitrogen; cellulose acetate, which has a very high permeability to water and carbon dioxide and a very poor permeability to oxygen and nitrogen; polyurethane, which has a very good permeability to water and a reasonably good permeability to carbon dioxide; ethylene-vinyl acetate copolymer, which has a very high permeability to carbon dioxide and a moderate permeability to oxygen; certain ionomers, on the other hand, are highly permeable to oxygen but hardly permeable to other gases. These are just general outlines of information and it should be taken into consideration that the permeability of polymers can be changed by modifying the chemical structure thereof and, therefore, the above list should by no means be considered as limiting the number of applicable materials. Although it was pointed out earlier in this specification that the gas-permeable membrane materials 11, 13–15 should be selected to comprise membranes with a low elasticity, this is not inevitable since at least one of the permeable membrane materials can be elastic, especially if the impermeable second membrane material is non-elastic, as described above. Designing and preparing the first area A1, A3 of the wall 7 to cover less than 50%, i.e. for example 20%, 25% or 30%, of the surface area A1+A2, A3+A2 of the entire wall makes this possible and is a contribution to it. The second impermeable membrane material comprises some material as highly anti-diffusion as possible, such as particularly polyvinyldenichloride (PVDC), polychloride tetrafluoroethylene (PCTFE), polyethylene terephtalate (PTFE), polyvinyl alcohol (PVA), and in laminates naturally foil metals, such as a foil of aluminium.

Furthermore, in its distal end far from the guide means, the measuring head of the invention may be provided with self-forming holding elements 25a or a separate holding element 25b. See FIGS. 16 and 17. The self-forming holding element 25a is explicitly created by the above-described uneven distribution of the contact force Q between different individuals X1 and X2 at a measuring site, providing the distal end of a measuring head far from the guide means with an expansion, wherein the spacing T between the areas A1 and A2 is reasonably large. The development of this expansion is understandable in such a way that a major force Q focused on a given part of the measuring head displaces the measuring medium 20 within the chamber 1, 2 to other parts, as a result of which the chamber thickness T increases at the distal end while the width W decreases at the distal end. Such strains do not interfere e.g. with a childbirth, since the measuring medium is capable of aptly moving to various parts as the focal point of the most powerful compressive force changes. If it is known beforehand that a compression between the individuals X1 and X2 is well balanced, the distal end far from the guide means can be provided with some separate holding element 25b for preventing the measuring head from slipping off. In addition to this, the measuring head of the invention may contain other tonometrically independent detectors 42, such as temperature sensors, pH sensors or others, which are generally simplest to attach to some suitable part of the wall of the measuring head 100 and to extend the guides of this detector 42 to an external device the same way as the guide means 3. Such a separate detector 42, along with its wires, is shown with a dashed line in FIGS. 3–4.

The tonometric measuring head of the invention can be preferably used for monitoring non-invasively the prenatal and natal physical condition of a fetus or a presently delivered child i.e. child in delivery. The above-described asymmetrical measuring head of the invention includes an inactive side 8b, which was constituted by a substantially impermeable second membrane material 12, and an active side 8a, which was at least partially constituted by a membrane material 11, 13–15 highly permeable, and most of the time as highly permeable as possible, to at least one gas to be analyzed. Furthermore, the measuring head is very flat or has a thickness T which, in a direction perpendicular to this active side 8a and inactive side 8b, is very small, particularly in relation to the length L and width W of the measuring head. Such an elongated and flat measuring head is readily introducible between a birth/parturition canal 30 of a parturient or deliverer D and a child C presently in the birth canal, such that the measuring instrument has its active side 8a, including a first area A1, towards the child C and in contact with the child. The measuring head has its inactive side, including a second area A2, set in turn towards a wall of the birth/parturition canal 30, whereby no factors affecting the child monitoring results can be diffused from the parturient to the measuring medium 20 within the measuring head. When dealing with a childbirth, the measuring head is typically positioned in such a way that its length L reaches at least to some extent the area of a cervix uteri 31. This way, the measuring head is held security in position. In principle, the measuring head of the invention can be placed in some other position in the birth canal but, in this case, it is necessary to take into account the immobilization of the measuring head since, in these other cases, the pressure between the child and e.g. the wall of a corpus uteri 32 does not necessarily guarantee a sufficient immobility for the measuring head. This requires the use of the above-described additional elements 25b. At least in the case that the length L of a measuring instrument reaches at least at some point the area of the cervix uteri 31, the tonometric measuring head 100 of the invention holds at least at a sufficient accuracy its measuring position as a result of the mutual compressive force Q between the birth canal 30 and the child C. With the measuring head 100 placed this way and in this position, the active first area A1, constituted by the permeable membrane materials of the active side 8a, receives by way of diffusion from the child transcutaneously through this membrane material in the measuring medium 20 at least one gas G1 or G2 to be analyzed. Understandably, the inactive side 8b of a measuring head has an impermeability which denies harmful substances an access to the measuring medium 20 of the measuring head. Similarly, the second membrane material 12 of the inactive area eliminates also the effect of external factors on the composition of the measuring medium 20. The measuring head 100 of this invention is allowed to remain in the birth canal 30 between its wall and the child C. This is followed by analyzing the measuring medium contained in the chamber 1 for the concentration of a predetermined gas component either at fixed intervals or continuously, as described above, whereby the oxygen supply of a child can be monitored as an essentially continuous process and at a high precision.

Figure 15A:
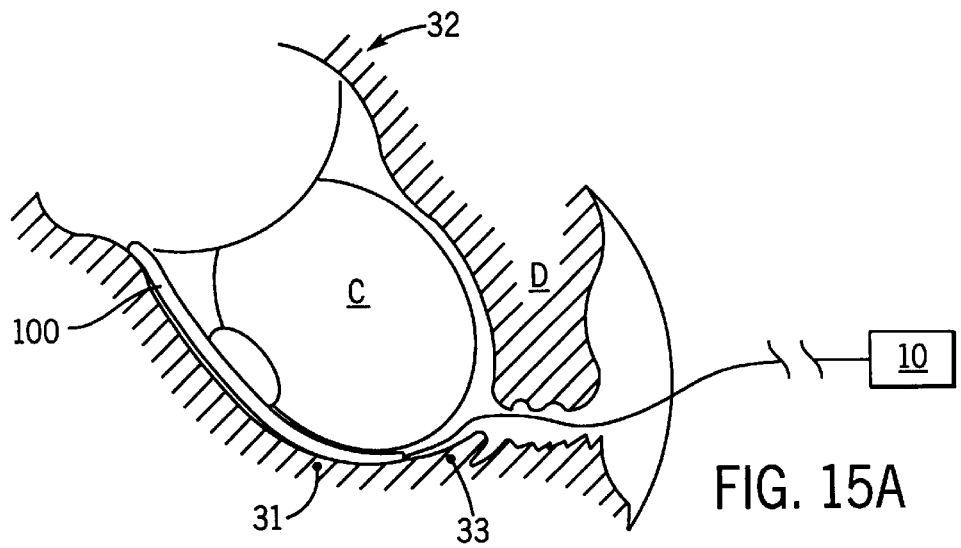
FIGS. 15A–15C illustrate schematically a presently delivered baby in a birth canal at various points and various conceivable positions for a measuring head of the invention in various phases of parturition.
Figure 15B:
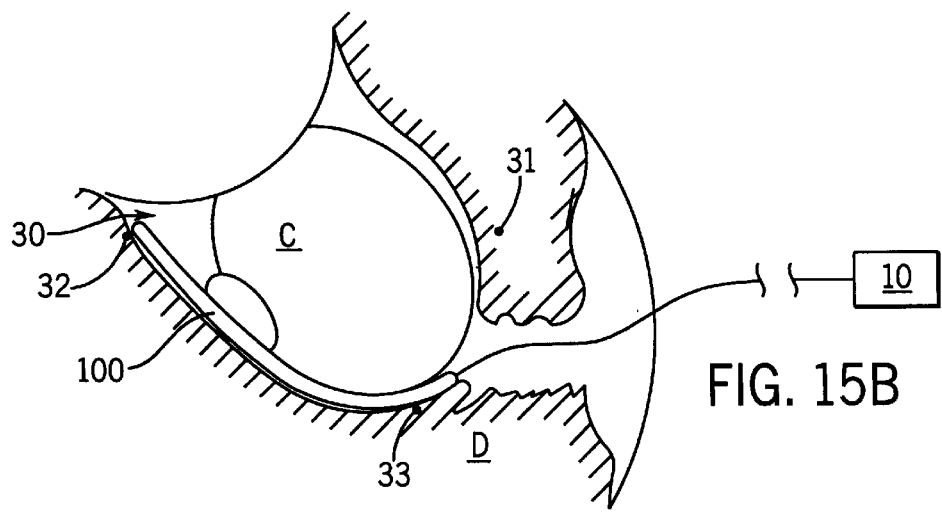
Figure 15C:
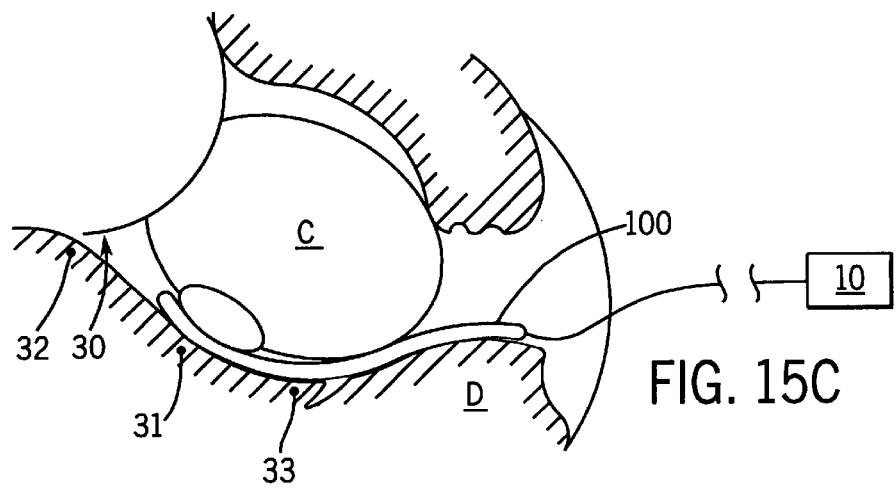

As pointed out above, the tonometric measuring head 100 of the invention may remain throughout parturition in the same position or it can be held in the same position. In addition to this, it is of course possible to shift the pliable chamber 1 of the measuring head, during the course of parturition, to various points within the birth canal 30 of the parturient D. Thus, the measuring head 100 can be initially positioned in such a way that it just barely extends from the area of the cervix uteri 31 towards the corpus uteri 32, such that most of the measuring head length is positioned between the corpus uteri 32 and the child C, as shown in FIG. 15A. As parturition progresses, the measuring head can be shifted in such a way that its length L now extends essentially from the region of the cervix uteri 31 both in the direction of corpus uteri 32 and in the direction of a orificium uteri 33, as shown in FIG. 15B. Furthermore, if necessary, the measuring head can be shifted to such a position that its length L extends just barely outwards from the region of the cervix uteri 31 and is mainly positioned between the orificium uteri 33 and the child C, as shown in FIG. 15C. It can be appreciated that a more accurate positioning for the measuring head 100 of the invention and a demand for shifting the measuring head are essentially dependent on whatever length L the measuring head has. It is not generally appropriate, however, that at least any substantial part of the length L of a measuring head would extend outwards from the orificium uteri 33, as this would increase a risk of ambient air causing a measuring error. It is obvious that the flexible guide means 3, 4, 5, 6 starting from the pliable chamber 1 of the measuring head 100 of the invention are adapted to extend away from the chamber 1 from its proximal end of the chamber closer to the orificium uteri, as shown in FIGS. 15A–15C. Thus, the guide means are extensible without any trouble to the external device 10. As described above in reference to the actual measuring head 100, the measuring medium 20 present within the chamber can be carried along the guide means 3, i.e. the tube 3a, to the external device 10 for analyzing the gases G1, G2 with the detecting elements 40 and back again along the guide means 3 to within the chamber. Optionally, the measuring medium 20 can be circulated along the guide means 3, 4 through the external device 10 as a continuous process. Of course, as described above, it is possible to analyze the measuring medium 20 with the detecting elements 41 inside the measuring chamber 1 for the concentration of the gas G1, G2 to be measured.

Figure 16:
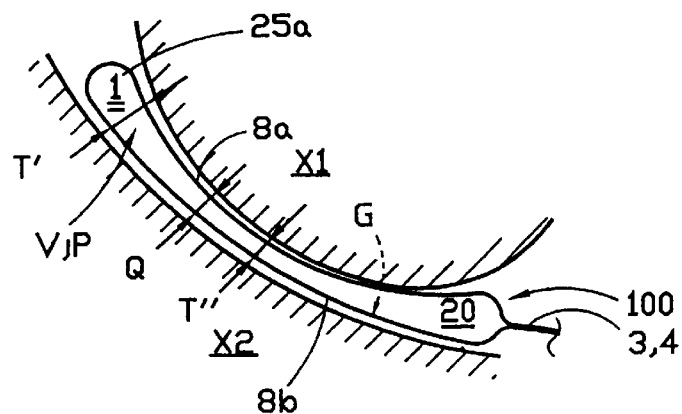
FIG. 16 shows one, more precise setting and holding for a measuring head of the invention in a contact situation between two individuals, such as in parturition, and in a view similar to FIGS. 15A–15C.
Figure 17:
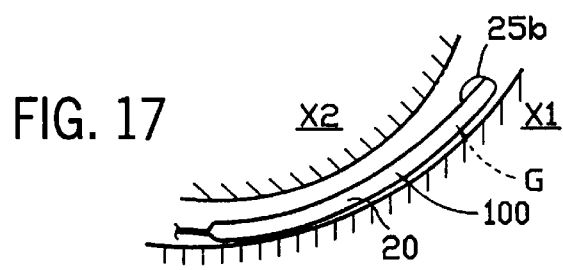
FIG. 17 shows a second, more precise setting and holding for a measuring head of the invention in a contact situation between two individuals, such as in parturition, and in a view similar to FIGS. 15A–15C.

In this case, during parturition, the measuring medium 20 in the cavity 9 of the pliable or flexible measuring head 100 is maintained for a preset or properly judged period of time in a condition to contain such a gel volume or a fluid volume V or a gas pressure P that said medium receives transcutaneously by way of diffusion from the child C a gas concentration to be measured. In reference to FIG. 16, this means that the measuring chamber 1 is maintained at a pressure or a measuring medium volume which establishes preferably at least a small spacing T'" between the opposite sides 8a and 8b within the region of the strongest compressive force Q between the child C or the first individual X1 and the birth canal wall of the parturient D or the second individual X2. In any event, the chamber 1 is maintained at such a volume or pressure that the surface area, over which the opposite sides of the chamber 1 are in contact with each other, is as small as possible in order to achieve a sufficient diffusion into the measuring medium 20. If, at some measuring site, the contact or compressive force between the first individual X1 and the second individual X2 is very balanced and quite insignificant, as shown in FIG. 17, it is perhaps necessary to employ other measuring head holding instruments.

The measuring head 100 of the invention can be used not only for monitoring the physical condition of the child C but also simultaneously for monitoring the physical condition of the parturient D, whereby both individuals X1 and X2 can thus be monitored concurrently, continuously, and independently of each other. This is carried out by using the above-described measuring head of the invention, comprising also a second sealed chamber 2 which also contains a measuring medium 20 and the like of which is depicted in FIGS. 8–10. As such a measuring head is positioned in the birth canal 30 in such a way that the active side 8a of this second chamber 2 has its active third area A3, constituted e.g. by a fourth membrane material 14 and possibly by a fifth membrane material 15, set towards the parturient D. Thus, through the outer cell layer of the body of the parturient D, in this case through the outermost cell layer of the birth canal 30, diffuses a subsequently analyzed gas into the measuring medium 20 present in this second chamber 2. This measuring medium can be analyzed for a desired gas or desired gases G3, G4, as described above. In this solution, the second membrane material 12 present between the first chamber 1 and the second chamber 2 includes an impermeable area A2 which prevents the contents of the first chamber 1 and the factors prevailing on the side of the first individual X1, in this case the child C, from affecting the second sealed chamber 2 and the measuring medium present therein. Inversely, the impermeable area A2 of this intermediary second membrane material 12 prevents the contents of the second chamber 2 and the factors prevailing on the side of the second individual X2, in this case the parturient D, from affecting the first sealed chamber 1.

It is obvious that this measuring head 100 of the invention can be used in any circumstances for measuring the concentration of any diffusible substance, i.e. generally a gas or a gasifiable substance, through a surface while simultaneously eliminating the effect of disturbing components coming from the opposite direction. Thus, in principle, the measuring head of the invention can be used for monitoring the physical condition of just a single individual X1 as well, as long as the active side 8a of the measuring head has its first area A1 tightly against this single individual only. This can be implemented e.g. in such a way that a measuring head of the invention is secured by means of an adhesive tape along its edges to the surface of an individual to be measured. Hence, the inactive side 8b of the measuring head has its impermeable and thus inactive second area A2 eliminate the impact of the environment. This way, the environment of an individual X1 to be measured can be regarded as a second individual, in this case a virtual individual X2. However, the best possible result is provided by the measuring head of the invention in a contact situation between two real-life individuals X1 and X2. There are a number of such contact situations between individual humans and individual animals. In principle, some of these are shown in FIGS. 16 and 17. It should further be noted that a measurement by way of the active side 8a of a measuring head can be effected either through the actual skin of an individual, i.e. transcutaneously, but also through mucous membranes or any accessible tissue surface. In human beings and animals, such other tissue layers include mucous membranes, internal uterine surface, various internal surfaces in digestive organs, and also various tissue surfaces appearing during surgery. If necessary, all of these can be utilized by making use of a measuring head of the invention.

What is claimed is:

1. A method for non-invasively monitoring a physiological condition of a child during parturition, said method comprising the steps of:

introducing an elongated, flat, pliant chamber member between the child (C) and the birth canal (30) of the parturient (D) with a first face wall of the chamber member facing the child and a second face wall of the chamber member facing the birth canal, said first face wall having an area (A1) formed of a first pliant material (11) permeable to a selected gas but effectively impermeable to at least liquids and solids, said second face wall having an area (A2) formed of a second pliant material (12) that is substantially impermeable both to the selected gas and to at least liquids and solids, the chamber member having a chamber containing a measuring medium;

retaining the chamber member in the birth canal by the action of the mutual compressive force (Q) between the birth canal (30) and the child (C);

allowing the selected gas to transfer from the child into the measuring medium in the chamber member across the area (A1) of the first pliant material while transfer of the selected gas over the area (A2) of the second pliant material is prevented to eliminate effects of the parturient (D) and external factors on the composition of the measuring medium; and analyzing the measuring medium contained in the chamber member to obtain the concentration of the selected gas to determine a physical condition of the child.

2. A method as set forth in claim 1 further defined as positioning the chamber member in the birth canal so that a portion of the chamber member reaches the area of the cervix uteri and as retaining the chamber member in position in the birth canal by the action of the mutual compressive force (Q) between the birth canal (30) and the child (C).

3. A method as set forth in claim 2 wherein said pliant chamber member is positioned in such a way that a substantial portion thereof extends from the cervix uteri (31) to between the corpus uteri (32) and the child and a lesser portion extends from the cervix uteri towards the orificium uteri (33), and wherein the pliant chamber means is provided with a flexible coupling member projecting therefrom and adapted to extend away from the chamber member from the end of the chamber member adjacent 4. A method as set forth in claim 2 wherein the chamber member is retained in the birth canal for a sufficient period of time during parturition for the measuring medium to receive an analyzable concentration of the selected gas for determining a physical condition of the child.

5. A method as set forth in claim 1 further defined as altering the position of the chamber member in the birth canal during parturition.

6. A method as set forth in claim 5 wherein said chamber member initially introduced so that the chamber member is essentially located between the corpus uteri (32) and the child (C), and wherein as parturition progresses, the chamber member is displaced along the birth canal (30) so that at least a portion of the chamber member extends beyond the orificium uteri (33).

7. A method as set forth in claim 1 further defined as removing the measuring medium from the chamber member to an external device for analyzing the measuring medium for the selected gas.

8. A method as set forth in claim 7 further defined as intermittently removing the measuring medium from the chamber member.

9. A method as set forth in claim 7 further defined as continously recirculating the measuring medium between the chamber member and the external device.

10. A method as set forth in claim 1 further defined as analyzing the measuring medium within the chamber member.

11. A method as set forth in claim 1 further defined as introducing a chamber member having a third pliant material, said third pliant material being permeable to a second gas to be analyzed but effectively impermeable to at least liquids and solids; and the analyzing step is further defined as analyzing the measuring medium contained in the chamber member to obtain the concentration of the second gas to determine a physiological condition of the child.

12. A method as set forth in claim 1 further defined as introducing an elongated, flat, pliant chamber member having a second chamber having a further face wall facing the birth canal, said further face wall having an area (A3) formed of a third pliant material (14) permeable to a selected gas but effectively impermeable to at least liquids and solids, said second chamber containing a second measuring medium;

allowing the selected gas to transfer from the birth canal of the parturient across the area (A3) of the third pliant material into the second measuring medium; and analyzing the second measuring medium contained in the second chamber to obtain the concentration of the selected gas to determine a physiological condition of the parturient.

13. A tonometric measuring head which is appliable to a tissue surface of an individual to be examined for allowing transfer of gas from the tissue surface to a measuring medium in the head so that the gas may be analyzed to determine a physiological condition of the individual, said measuring head comprising:

a chamber meber having opposing, sheet-like first and second face walls that form the chamber member into a generally flat, pad-like element having an internal chamber for receiving the measuring medium, each of said opposing face walls being formed of a pliant material for providing flexibility to said chamber member to allow deformation of said chamber member when said measuring head is in use so that a first face wall of said wall member may be applied to the tissue surface, said first face wall having a first area (A1) formed of a first pliant material (11) permeable to a gas to be analyzed but effectively impermeable to at least liquids and solids, and second face wall having aa second area (A2) formed of a second pliant material that is substantially impermeable both to the gas to be analyzed and to at least liquids and solids so that transfer of the gas to be analyzed occurs only in said first area (A1) of said first face wall;

detecting means in said chamber of said chamber member; and an elongated coupling means extending away from said chamber for use in the analysis of the measuring medium, said coupling means having first and second ends, said first end being joined to said chamber member, said coupling means containing signal transmitting means extending to said second end of said coupling means.

14. A tonometric measuring head which is appliable to a tissue surface of an individual to be examined for allowing transfer to gas from the tissue surface to a measuring medium in the head so that the gas may be analyzed to determine a physiological condition of the individual, said measuring head comprising:

a chamber member having opposing, sheet-like first and second face walls that form the chamber member into a generally flat, pad-like element having an internal chamber for receiving the measuring medium, each of said opposing face walls being formed of a pliant material for providing flexibility to said chamber member to allow deformation of said chamber member when said measuring head is in use so that a first face wall of said wall member may be applied to the tissue surface, said first face wall having a first area (A1) formed of a first pliant material (11) permeable to a first gas (G1) to be analyzed but effectively impermeable to at least liquids and solids, said first area (A1) being further formed of a third pliant material (13) which is permeable to a second gas (G2) to be analyzed but effectively impermeable to at least liquids and solids, said second face wall having a second area (A2) formed of a second pliant material that is substantially impermeable both to the gas to be analyzed and to at least liquids and solids so that transfer of a gas to be analyzed occurs only in said first area (A1) of said first face wall; and an elongated coupling means extending away from said chamber for use in the analysis of the measuring medium, said coupling means having first and second ends, said first being being joined to said chamber member.

15. A tonometric measuring head as set forth in claim 14 wherein said first pliant material is highly permeable to carbon dioxide and said third pliant material is highly permeable to oxygen.

16. A tonometric measuring head as set forth in claim 14 wherein said first pliant material is located in the proximal end of said measuring head with respect to said coupling means and wherein said third pliant material is located in the distal end of said measuring head with respect to said coupling means.

17. The tonometric measuring head which is appliable to a tissue surface of an individual to be examined for allowing transfer of gas from the tissue surface to a measuring medium in the head so that the gas may be analyzed to determine a physiological condition of the individual, said measuring head comprising:

a chamber member having opposing, sheet-like first and second face walls that form the chamber member into a generally flat, pad-like element having an internal chamber for receiving the measuring medium, each of said opposing face walls being formed of a pliant material for providing flexibility to said chamber member to allow deformation of said chamber member when said measuring head is in use so that a first face wall of said wall member may be applied to the tissue surface, said first face wall having a first area (A1) formed of a first pliant material (11) permeable to a gas to be analyzed but effectively impermeable to at least liquids and solids, said second face wall having a second area (A2) formed of a second pliant material that is substantially impermeable both to the gas to be analyzed and to at least liquids and solids so that transfer of the gas to be analyzed occurs in said first area (A1) of said first face wall, said chamber member further including a third sheet-like face wall for forming a further chamber in said chamber member on the opposite said of said second face wall from said chamber formed by said first and second face walls for receiving a measuring medium, said third face wall being appliable to another tissue surface and having a third area (A3) formed of a fourth pliant material which is permeable to a gas to a analyzed occurs in said third area (A3) of said third face wall; and an elongated coupling means extending away from said chamber for use in the analysis of the measuring medium, said coupling means having a first and second ends, said first end being joined to said chamber and further chamber of said chamber member.

18. A tonometric measuring head as set forth in claim 17 wherein said third area (A3) is further defined as comprised of a fifth pliant material which is permeable to a fourth gas (G4) to be analyzed but is effectively impermeable to at least solids and liquids.

19. A tonometric measuring head as set forth in claim 17 wherein said first and second face walls form a wall area for the chamber in said chamber member, wherein said second and third face walls form a wall area for said further chamber in said chamber member, and wherein said second area (A2) formed by said second pliant material makes up at least 40% of the wall areas of said chamber and further chamber.

20. A tonometric measuring head as set forth in claim 19 wherein said second area (A2) formed by said second pliant material makes up at least 50% of the wall area of the chamber and the wall area of the further chamber.

21. A tonometric measuring head as set forth in claim 20 wherein said second area (A2) formed of said second pliant material makes up not more than 70% of the wall area of the chamber and the wall area of the further chamber.

22. A tonometric measuring device as set forth in claim 17 wherein said coupling means comprises a tube (3a) having at least one flow channel (3b), said tube being substantially impermeable to gases, liquids, and solids, said first end of said coupling means placing said flow channel in fluid communication with at least one of said chamber and further chamber of said chamber member, said second end of said coupling means discharging measuring medium containing gas transferred from the tissue surface of the individual, said flow channel supplying and receiving the measuring medium to and from said at least one of said chamber and further chamber of said chamber member.

23. A tonometric measuring head as set forth in claim 17 wherein said coupling means includes a first tube (3a) including a first flow channel, said tube being substantially impermeable to gases, liquids, and solids, said first end of said first flow channel being in fluid communication with at least one of said chamber and further chamber of said chamber member, said first tube having a second end, said coupling means further including a second tube (4a) having a second flow channel (4b), said second tube being substantially impermeable to gases, liquids, and solids, a first end of said second flow channel being in fluid communication with said at least one of said chamber and further chamber of said chamber member, said second tube having a second end, wherein said first and second tubes permit a measuring medium to circulate through said at least one of said chamber and further chamber of said chamber member by supplying measuring medium through one of said tubes and discharging measuring medium through the other of said tubes.

24. A tonometric measuring head which is appliable to a tissue surface of an individual to be examined for allowing transfer of CO2 gas from the tissue surface to a measuring medium in the head so that the gas may be analyzed to determine a physiological condition of the individual, said measuring head comprising:

a chamber member having opposing, sheet-like first and second face walls that form the chamber meber into a generally flat, pad-like element having an internal chamber for receiving the measuring medium, each of said opposing face walls being formed of a pliant material for providing flexibility to said chamber member to allow deformation of said chamber member when said measuring head is in use so that a first face wall of said wall member may be applied to the tissue surface, said first face wall having a first area (A1) formed of a first pliant material (11) permeable to CO2 gas but effectively impermeable to at least liquids and solids, and second face wall having a second area (A2) formed of a second pliant material that is substantially impermeable both to the CO2 gas to be analyzed and to at least liquids and solids so that transfer of the gas to be analyzed occurs only in said first area (A1) of said first face wall; and an elongated coupling means extending away from said chamber for use in the analysis of the measuring medium, said coupling means having first and second ends, said first end being joined to said chamber member.

25. A tonometric measuring decive as set forth in claim 14, or 24 wherein said coupling means comprises a tube (3a) having at least one flow channel (3b), said tube being substantially impermeable to gases, liquids, and solids, said first end of said coupling means placing said flow channel in fluid communication with said chamber of said chamber member, said second end of said coupling means discharging measuring medium containing gas transferred from the tissue surface of the individual, said flow channel supplying and receiving the measuring medium to and from said chamber of said chamber member.

26. A tonometric measuring head as set forth in claim 14, or 24 wherein said coupling means includes a first tube (3a) including a first flow channel, said tube being substantially impermeable to gases, liquids, and solids, said first end of said first flow channel being in fluid communication with said chamber of said chamber member, said first tube having a second end, said coupling means further including a second tube (4a) having a second flow channel (4b), said second tube being substantially impermeable to gases, liquids, and solids, a first end of said second flow channel being in fluid communication with said chamber of said chamber member, said second tube having a second end, wherein said first and second tubes permit a measuring medium to circulate through said chamber of said chamber member by supplying measuring medium through one of said tubes and discharging measuring medium through the other of said tubes.

27. A tonometric measuring head as set forth in claim 14, 17, or 24 further defined as suitable for use with a measuring medium comprising a liquid, gel, or a gaseous medium.

28. A totometric measuring head as set forth in claim 14, 17, or 24 further including said measuring medium, said measuring meadium comprising a liquid, gel, or gaseous measuring medium.

29. A tonometric measuring head as set forth in claim 14, 17, or 24 further including a detecting element (40, 41) exposed to the measuring medium containing the gas to be analyzed transferred from the tissue surface for determining the concentration of the gas transferred from the tissue surface.

30. A tonometric measuring head as set forth in claim 13 or 24 wherein said measuring head includes at least one detector operatively associated therewith for detecting a property other than gas to be analyzed.

31. A tonometric measuring head which is appliable to a tissue surface of an individual to be examined for allowing transfer of gas from the tissue surface to a measuring medium in the head so that the gas may be analyzed to determine a physiological condition of the individual, said measuring head comprising:
- a chamber member having opposing, sheet-like first and second face walls that form the chamber meber into a generally flat, pad-like element having an internal chamber for receiving the measuring medium, each of said opposing face walls being formed of a pliant material for providing flexibility to said chamber member to allow flexing of said chamber member when said measuring head is applied to the tissue surface so that a first face wall of said wall member may be applied to the tissue surface, said first face wall having a first area (A1) formed of a first pliant material (11) permeable to a gas to be analyzed by effectively impermeable to at least liquids and solids, said second face wall having a second area (A2) formed of a second pliant material which is substantially impermeable to both the gas to be analyzed and to at least liquids and solids so that transfer of the gas to be analyzed occurs only in said first area (A1) of said first face wall, at least said second pliant material being substantially non-elastomeric:
- an elongated coupling means extending away from said chamber for use in the analysis of the measuring medium, said coupling means having first and second ends, and first end being joined to said chamber member.

32. A tonometric measuring head as set forth in claim 14, 17, 24, or 31 wherein said elongated coupling means is flexible.

33. A tonometric measuring head as set forth in claim 14, 17, or 31 wherein said first and second face walls from a wall area for said chamber member and wherein said second area (A2) formed by said second pliant material makes up at least 40% of the wall area of said chamber member.

34. A tonometric measuring head as set forth in claim 15 wherein said second area (A2) makes up at least 50% of the wall area of said chamber member.

35. A tonometric measuring head as set forth in claim 14, 17, or 31 wherein said first and second face walls form a wall area for said chamber member and wherein said second area (A2) formed of said second pliant material makes up not more than 80% of the wall area of said chamber.

36. A tonometric measuring head as set forth in claim 17 wherein said seond pliant material is a laminate containing a layer providing impermeability to said laminate.

37. A tonometric measuring head as set forth in claim 17, 24, or 31 wherein said first pliant material is formed of a single type of material and wherein said second pliant material is formed of one of a single type of material and a laminate of different materials.

38. A tonometric measuring head as set forth in claim 38 wherein said second pliant material is a laminate containing a layer providing impermeability to said laminate.

39. A tonometric measuring head as set forth in claim 37 wherein said second pliant material is a laminate containing a layer providing reduced elasticity to said laminate.

40. A tonometric measuring head as set forth in claim 17, 24, or 31 wherein said pliant materials have a thickness of not more than 0.2 mm.

41. A tonometric measuring head as set forth in claim 40 wherein said pliant materials have a thickness of not more than 0.1 mm.

42. A tonometric measuring head as set forth in claim 41 wherein said pliant materials have a thickness of not more than 0.05 mm.

43. A tonometric measuring head as set forth in claim 42 wherein said chamber has an average spacing (T) between said opposing face walls when filled with measuring medium of not more than 5 mm.

44. A tonometric measuring apparatus as set forth in claim 43 wherein said average spacing is not more than 2 mm.

45. A tonometric measuring head as set forth in claim 43 wherein the average spacing between said opposing face walls is on the order of 1 mm.

46. A tonometric measuring head as set forth in claim 17, 24, or 31 wherein said first pliant material has a thickness in a range of 0.03 mm–0.01 mm.

47. A tonometric head as set forth in claim 14, 17, 24, or 31 wherein said chamber member has a length in a range of 2 cm–20 cm, a width in a range of 1 cm–10 cm.

48. A tonometric measuring head as set forth in claim 47 wherein the ratio of the length of said chamber member to the width of said chamber member is in a range of 1:1.5 to 1:5.

49. A tonometric measuring head as set forth in claim 31 wherein said first and second pliant materials are joined to each other in a flexible manner.

50. A tonometric measuring head as set forth in claim 24 or 31 wherein said chamber of said chamber member contains one or more partitions connecting said opposing face walls for forming a channel in said chamber for a measuring medium provided by said coupling means.

51. A tonometric measuring head as set forth in claim 20 wherein said one or more partitions form a serpentine channel in said chamber.

52. A tonometric measuring head as set forth in claim 24 or 31 wherein said chamber of said chamber member contains a fibrous or open cell material affixed to said face walls for receiving the measuring medium.

53. A tonometric measuring head as set forth in claim 31 wherein said first and second pliant materials are substantially non-elastomeric.

54. A tonometric measuring device as set forth of claim 31 or 53 wherein said non-elastomeric property of said pliant material or materials is porivded by forming said material or materials from a non-elastic pliant material or from a laminate of a non-elastoc mesh amd elastic material.

55. A tonometric measuring head as set forth in claim 14, 17, 24, or 31 wherein said chamber is characterized by an absence of internal supports.

56. A tonometric measuring head which is appliable to a tissue surface of an individual to be examined for allowing transfer of gas from the tissue surface to a measuring medium in the head so that the gas may be analyzed to determine a physiological condition of the individual, said measuring head comprising:
- a chamber member having opposing, sheet-like first and second face walls that form the chamber member into a generally flat, pad-like element having an internal chamber for receiving the measuring medium, each of said opposing face walls being formed of a pliant material for providing flexibility to said chamber member to allow deformation of said chamber member when said measuring head is in use so that a first face wall of said wall member may be applied to the tissue surface, said first face wall having a first area (A1) formed of a first pliant material (11) permeable to a gas to be analyzed but effectively impermeable to at least liquids and solids, said second face wall having a second area (A2) formed of a second pliant material that is substantially impermeable both to the gas to be analyzed and to at least liquids and solids so that transfer of the gas to be analyzed occurs only in said first area (A1) od said first face wall, said chamber member including holding elements (25a, 25b) for positioning the measuring head on the tissue surface; and an elongated coupling means extending away from said chamber for use in the analysis of the measuring medium, said coupling means having first and second ends, said first end being joined to said chamber member.

\* \* \* \* \*

UNITED STATES PATENT AND TRADEMARK OFFICE
CERTIFICATE OF CORRECTION

PATENT NO. : 6,432,051 B1
DATED : August 13, 2002
INVENTOR(S) : Börje T. Rantala It is certified that error appears in the above-identified patent and that said Letters Patent is hereby corrected as shown below:

<u>Title page,</u>
Item [75], should read:
-- [75]   Inventor:        Börje T. Rantala --

<u>Column 22,</u>
Line 57, after "adjacent" insert -- to the orificium uteri --
Line 67, after "member" insert -- is --

<u>Column 23,</u>
Line 48, delete "meber" and substitute therefor -- member --
Line 60, delete "and" and substitute therefor -- said --
Line 60, delete "aa" and substitute therefor -- a --

<u>Column 24,</u>
Line 10, delete "to" and substitute therefor -- of --
Line 39, after "first" insert -- end --

<u>Column 25,</u>
Line 10, delete "said" in first occurrence and substitute therefor -- side --
Line 15, delete "a" in the second occurrence and substitute therefor -- be --
Line 15, after "analyzed" insert -- but substantially impermeable to liquids and solids so that transfer of gas to be analyzed --

<u>Column 26,</u>
Line 14, delete "meber" and substitute therefor -- member --
Line 25, delete "and" and substitute therefor -- said --
Line 35, delete "decive" and substitute therefor -- device --
Line 66, delete "totometer" and substitute therefor -- tonometer --

<u>Column 27,</u>
Line 20, delete "meber" and substitute therefor -- member --
Line 30, delete "by" and substitute therefor -- but --
Line 33, delete "which" and substitute therefor -- that --
Line 33, delete "to both" and substitute therefor -- both to --
Line 41, delete "and" and substitute therefor -- said --
Line 45, delete "from" and substitute therefor -- form --

UNITED STATES PATENT AND TRADEMARK OFFICE
CERTIFICATE OF CORRECTION

PATENT NO.    : 6,432,051 B1
DATED         : August 13, 2002
INVENTOR(S)   : Börje T. Rantala It is certified that error appears in the above-identified patent and that said Letters Patent is hereby corrected as shown below:

<u>Column 28,</u>
Line 27, after "tonometric" insert -- measuring --
Line 52, delete "proivded" and substitute -- provided --
Line 54, delete "non-elastoc" and substitute therefor -- non-elastic --

<u>Column 30,</u>
Line 2, delete "od" and substitute therefor -- of --

Signed and Sealed this

Fifteenth Day of April, 2003

JAMES E. ROGAN
*Director of the United States Patent and Trademark Office*